US012740963B2

(12) United States Patent
Stains et al.

(10) Patent No.: US 12,740,963 B2
(45) Date of Patent: Sep. 22, 2026

(54) METHODS FOR TREATING BONE-RELATED DISORDERS

(71) Applicants: Joseph Stains, Laurel, MD (US); Christopher Ward, Baltimore, MD (US); James Lyons, York, PA (US)

(72) Inventors: Joseph Stains, Laurel, MD (US); Christopher Ward, Baltimore, MD (US); James Lyons, York, PA (US)

(73) Assignee: University of Maryland, Baltimore., Baltimore, MD (US)

( * ) Notice: Subject to any disclaimer, the term of this patent is extended or adjusted under 35 U.S.C. 154(b) by 1135 days.

(21) Appl. No.: 17/745,556

(22) Filed: May 16, 2022

(65) Prior Publication Data

US 2022/0273608 A1 Sep. 1, 2022

Related U.S. Application Data

(63) Continuation-in-part of application No. 16/461,555, filed as application No. PCT/US2017/062033 on Nov. 16, 2017, now abandoned.

(60) Provisional application No. 62/422,717, filed on Nov. 16, 2016.

(51) Int. Cl.

| | |
|---|---|
| ***A61K 31/165*** | (2006.01) |
| ***A61K 31/337*** | (2006.01) |
| ***A61K 39/395*** | (2006.01) |
| ***A61P 19/08*** | (2006.01) |
| ***C07K 16/22*** | (2006.01) |

(52) U.S. Cl.

CPC .......... *A61K 31/337* (2013.01); *A61K 31/165* (2013.01); *A61K 39/3955* (2013.01); *A61P 19/08* (2018.01); *C07K 16/22* (2013.01); *C07K 2317/24* (2013.01)

(58) Field of Classification Search

CPC ..... A61K 31/165; A61K 31/337; A61K 19/08

See application file for complete search history.

(56) References Cited

U.S. PATENT DOCUMENTS

2015/0164831 A1* 6/2015 Roberts .................. A61K 9/501
424/490

OTHER PUBLICATIONS

McClung et al., N. Engl. J. Med., 2014, vol. 370:412-420.*

* cited by examiner

*Primary Examiner* — Xiaozhen Xie

(74) *Attorney, Agent, or Firm* — Benjamin Aaron Adler

(57) ABSTRACT

Provided herein are methods for treating a bone-related disorder in a subject. At least one of a microtubule altering drug, for example, a microtubule disrupting drug or a microtubule stabilizing drug, a TRPV4 agonist or a NOX2 activator is administered to the subject. Also provided are related methods for treating a bone-related disorder in the subject by further administering at least one of an anti-sclerostin agent, a parathyroid hormone agonist, a bisphosphonate, an estrogen mimic, or a selective estrogen receptor modulator with the at least one of a microtubule altering drug, a TRPV4 agonist or a NOX2 activator.

15 Claims, 23 Drawing Sheets

ΔF/F
10 sec
control
colchicine
4 dynes/cm²
Time to peak (sec)
% Cells Responding
100
80
60
40
1
0
control
colchicine
***
Peak (ΔF/F)
1.5
1.0
0.5
0.0
control
colchicine
***

1 δF/F
10 sec
control
colchicine
16 dynes/cm²
Time to peak (sec)
% Cells Responding
100
80
60
40
20
0
control
colchicine
**
Peak (ΔF/F)
2.0
1.5
1.0
0.5
0.0
control
colchicine
** control
taxol
No FSS
4 dynes/cm$^2$
16 dynes/cm$^2$
sclerostin
p-CamKII
total-CamKII
GAPDH
Sclerostin/GAPDH
p-CamK/t-CamK
ns
16 dynes/cm$^2$ Osteocytes *in Situ*

1 δF/F
10 sec
control
PTL
4 dynes/cm²
Time to peak (sec)
%Cells Responding
100
80
60
40
20
0
control
PTL
Peak (ΔF/F)
1.5
1.0
0.5
0.0
control
PTL

METHODS FOR TREATING BONE-RELATED DISORDERS

CROSS-REFERENCE TO RELATED APPLICATIONS

This application is a continuation-in-part application of U.S. Ser. No. 16/461,555, filed May 16, 2019 (now abandoned), which is a national stage application under 35 U.S.C § 371 of international patent application PCT/US2017/062033, filed Nov. 16, 2017, which claims benefit of priority under 35 U.S.C. § 119 (e) of provisional application U.S. Ser. No. 62/422,717, filed Nov. 16, 2016, the entirety of all of which is hereby incorporated by reference.

STATEMENT OF GOVERNMENT SUPPORT

This invention was made with the government support under Grant No. § 063631 awarded by the National Institutes of Health. The Government has certain rights in the invention.

BACKGROUND OF THE INVENTION

Field of the Invention

The invention relates generally to the field of medicine and in particular methods for modulating the microtubule network in bone formation pathways as a therapeutic strategy for improving or preserving bone mass in aging and disease.

Description of the Related Art

Osteoporosis is a disease characterized by significantly low bone mass and/or low bone quality with increased fracture risk. It is a disease that is seen in the elderly, post menopausal women, and patients with limited mobility (for example, bed ridden), but also in healthy patents that for example spend extended amounts of time in zero gravity (space flight). Bone quality is maintained through the constant formation and destruction of bone. Mechanical load is a key regulator of bone. Osteocytes embedded within the bone sense external mechanical load and respond by altering gene expression and protein bioavailability of factors that play a role in regulating the balance of bone formation and destruction. Accumulating evidence suggests that mechanotransduction pathways activate several signaling cascades and calcium (Ca2+) that play a role in the balance of bone formation and destruction. Preventing bone loss and/or restoring lost bone mass in patients is of vital importance to limiting the personal and economic impact of diseases of skeletal fragility.

Bone dynamically remodels to adapt to mechanical loads to maintain its structural integrity. Bone-embedded osteocytes, residing in the fluid filled lacunar-canalicular system, are central to skeletal mechano-responsiveness. In response to mechanical load, osteocytes experience fluid shear stress (FSS), which triggers calcium ($Ca^{2+}$), extracellular ATP, nitric oxide, and PGE2 signals and orchestrate bone remodeling through effector molecules, such as sclerostin, RANKL and osteoprotegerin. These effectors act on bone forming osteoblasts and bone resorbing osteoclasts to add, remove and replace bone to accommodate mechanical demands. Sclerostin (which is encoded by Sost) is an osteocyte-specific secreted glycoprotein that suppresses bone formation by antagonizing canonical Wnt-β-catenin signaling, reducing osteoblast differentiation, and bone formation. In an important response to mechanical load, osteocytes reduce sclerostin abundance, leading to "de-repression" of osteoblastogenesis and stimulation of de novo bone formation.

In humans, Sost deficiency leads to the high bone mass disorders sclerosteosis and van Buchem disease, and genetic ablation of Sost in mice results in increased bone mass. Although therapeutically targeting sclerostin is effective at improving bone quality in animal models and in humans, the mechanotransduction pathways linking fluid shear stress to the decrease in sclerostin abundance remain undefined. Similarly, despite the mechano-responsive nature of osteocytes, the identity of the "mechano-sensor" is controversial. Furthermore, while integrin-associated mechanosomes, osteocyte cell processes, primary cilia and connexin43 hemichannels have been implicated as mechano-sensors and in mechano-activated $Ca^{2+}$ influx in bone cells, they have not been mechanistically linked to sclerostin downregulation.

The cytoskeleton, composed of microtubules (MT), actin and intermediate filaments, is a dynamic structure that forms an interconnected three-dimensional framework of molecular struts and cables within the cell. A growing body of evidence indicates that the cytoskeleton is critical for the cellular response to the mechanical environment, as it integrates and transduces mechanical energy to mechano-sensitive proteins that generate biological signals in various cell types.

MTs arise from the polymerization of α- and β-tubulin dimers. The MT network is a dynamic structure whose density and stability is regulated by post-translational modifications (such as detyrosination, acetylation and phosphorylation) and microtubule associated proteins (MAPs) that affect the equilibrium between MT filament growth, disassembly, and association with other cytoskeletal elements.

Thus, there is a recognized need in the art to identify molecules and methods which can modulate and affect bone quality so as to provide a means for treating and/or preventing bone loss and thus improving bone quality. The present invention fulfills this longstanding need and desire in the art.

SUMMARY OF THE INVENTION

The present invention is directed to a method for treating a bone-related disorder in a subject. In this method, an amount of a microtubule altering drug pharmacologically effective to treat the bone-related disorder is administered to the subject. The present invention is directed to a related method further comprising administering to the subject at least one of an anti-sclerostin agent, a parathyroid hormone agonist, a bisphosphonate, an estrogen mimic, or a selective estrogen receptor modulator.

The present invention is further directed to another method for treating a bone-related disorder in a subject. In this method, an amount of a microtubule disrupting drug, an amount of a microtubule stabilizing drug or a combination thereof, each pharmacologically effective to treat the bone-related disorder is administered one or more times to the subject.

The present invention is directed further to a method for increasing bone mass in a subject in need thereof. In this method, an amount of a microtubule disrupting drug pharmacologically effective to decrease sclerostin in the subject is administered one or more times thereto. The present invention is directed to a related method further comprising administering to the subject at least once a microtubule stabilizing drug or an anti-sclerostin agent or a combination thereof.

Other and further aspects, features, and advantages of the present invention will be apparent from the following description of the presently preferred embodiments of the invention given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1A shows $Ca^{2+}$ imaging of Ocy454 cells exposure to 4 dynes/$cm^2$ FSS. Pseudocolored images are shown. n=5 independent experiments. Scale bar, 100 μm. FIG. 1B shows $Ca^{2+}$ responses in Ocy454 cells exposed to 4 dynes/$cm^2$ fluid shear stress. Trace indicates Fluo-4 fluorescence changes over time. Average trace of all cells (>200 cells in n=3 independent experiments) shown in bold. Representative individual cell traces are shown in gray. % Cells Responding indicates number of cells with >25% increase in fluorescence. FIG. 1C shows untreated Ocy454 cells and BAPTA-AM ester loaded Ocy454 cells subjected to 4 dynes/$cm^2$ fluid shear stress with $Ca^{2+}$ containing or $Ca^{2+}$ free flow buffer, respectively. Immunoblotting was performed for p-CaMKII, total-CaMKII, sclerostin, and GAPDH (n=3 independent experiments). The sclerostin to GAPDH and p-CaMKII to total-CaMKII ratios are shown. FIG. 1D shows control Ocy454 cells and KN-93 treated Ocy454 cells subjected to 4 dynes/$cm^2$ fluid shear stress and immunoblotted for sclerostin and GAPDH (n=3 independent experiments). The sclerostin to GAPDH ratios are indicated. FIG. 1E shows Ocy454 cells, transfected with GFP control or CaMKII T286A constructs, and subjected to 4 dynes/$cm^2$ fluid shear stress, immunblotted for sclerostin and GAPDH (n=3 independent experiments). The sclerostin to GAPDH ratios are shown. Graphs depict mean±sem. p<0.001, *p<0.0001 versus control by Kruskal-Wallis test. ns, not significantly different.

FIG. 2A shows Ocy454 cells stained for α-tubulin (red), phalloidin (actin, green), and DAPI (nuclei, blue). Red arrows in inset depict α-tubulin in osteocyte cell process and primary cilia. Scale bar, 10 μm. n=3 independent experiments. FIG. 2B shows Murine femurs stained with SiR-tubulin. White arrows indicate MTs in the osteocyte cell processes in situ. Scale bar, 20 μm. n=3 mice. FIGS. 2C-2D show $Ca^{2+}$ response of Ocy454 cells treated with colchicine and subjected to 4 (FIG. 2C) or 16 (FIG. 2D) dynes/$cm^2$ fluid shear stress. Trace indicates average Fluo-4 fluorescence changes over time (>200 cells per treatment, n=3 independent experiments), % Cells Responding indicates number of cells with >25% increase in fluorescence, Peak(ΔF/F) indicates peak magnitude of $Ca^{2+}$ response. $Ca^{2+}$ data for control 4 dynes/$cm^2$ fluid shear stress are same trace shown in FIG. 1B, as these were run in parallel with colchicine interventions. FIG. 2E shows Ocy454 cells treated with colchicine subjected to 4 dynes/$cm^2$ fluid shear stress and immunoblotted for the indicated proteins. Sclerostin to GAPDH and p-CaMKII to total-CaMKII ratios are shown (n=3 independent experiments). Images are from a single exposure of a contiguous membrane. Dotted lines indicate the removal of irrelevant lanes. FIG. 2F shows immunostaining for α-tubulin in control and colchicine treated Ocy454 cells. Scale bar, 10 μm. n=3 independent experiments. Graphs depict mean±sem.  p<0.001, * p<0.0001 versus control by two tailed Mann-Whitney test (C,D) or Kruskal-Wallis test (E). ns, not significantly different.

FIGS. 3A-3B shows $Ca^{2+}$ response of Fluo-4 loaded Ocy454 cells treated with Taxol and subjected to 4 (FIG. 3A) or 16 (FIG. 3B) dynes/$cm^2$ fluid shear stress. Trace indicates average Fluo-4 fluorescence changes over time (>200 cells per treatment, n=3 independent experiments), % Cells Responding indicates number of cells with >25% increase in fluorescence, Peak(ΔF/F) indicates peak magnitude of $Ca^{2+}$ response. The $Ca^{2+}$ data for the controls at 4 and 16 dynes/$cm^2$ fluid shear stress are the same traces as in FIG. 1B and FIG. 2D, as these controls were run in parallel with the Taxol interventions. FIG. 3C shows control or Taxol treated Ocy454 cells subjected to fluid shear stress and immunoblotted for the indicated proteins. Sclerostin to GAPDH and p-CaMKII to total-CaMKII ratios are indicated (n=3 independent experiments). FIG. 3D shows immunostaining for α-tubulin in control and Taxol treated Ocy454 cells. Scale bar, 10 μm. n=3 independent experiments. Graphs depict mean±sem. * p<0.05,  p<0.001, * p<0.0001 versus control by two tailed Mann-Whitney test (FIGS. 3A, 3B) or Kruskal-Wallis test (FIG. 3C), ns, not significantly different.

FIG. 4A shows Ocy454 cells immunostained for α-tubulin (red), Glu-tubulin (green), and DAPI (blue). Osteocyte cell process and primary cilia are indicated by the red arrow and red arrowheads. Scale bar, 20 μm. n=3 independent experiments. FIG. 4B shows murine long bone sections immunostained for Glu-tubulin. Red arrows indicate Glu-tubulin in the osteocyte cell processes in situ. Scale bar, 50 μm. n=3 mice. FIG. 4C shows Ocy454 cells and ex vivo murine long bone treated with Taxol and immunoblotted for indicated proteins. Glu-tubulin to α-tubulin ratios are indicated (n=3 independent experiments). The image is from a single exposure of a contiguous membrane. Dotted lines indicate the removal of irrelevant lanes. FIG. 4D shows immunostaining for α-tubulin (red), Glu-tubulin (green) and DAPI (blue) in control and Taxol treated Ocy454 cells. Scale bar, 10 μm. n=3 independent experiments. FIGS. 4E-4F show the $Ca^{2+}$ response of Ocy454 cells treated with parthenolide (PTL) and subjected to 4 (FIG. 4E) or 16 (FIG. 4F) dynes/$cm^2$ fluid shear stress. Trace indicates average Fluo-4 fluorescence changes over time (>200 cells per treatment, n=3 independent experiments), % Cells Responding indicates number of cells with >25% increase in fluorescence, Peak(ΔF/F) indicates peak magnitude of $Ca^{2+}$ response. The $Ca^{2+}$ data for the controls at 4 and 16 dynes/$cm^2$ fluid shear stress are the same traces as in FIG. 1B and FIG. 2D, respectively, as these controls were run in parallel with the PTL interventions. FIG. 4G shows control or PTL treated Ocy454 cells subjected to fluid shear stress and immunblotted for indicated proteins. Sclerostin to GAPDH and p-CaMKII to total-CaMKII ratios are shown (n=3 independent experiments). FIG. 4H shows control Ocy454 cells or Ocy454 cells treated with PTL were immunostained for α-tubulin (red), Glu-tubulin (green), and DAPI (blue). n=3 independent experiments. Scale bar, 10 μm. Graphs depict mean±sem. p<0.001, *p<0.0001 versus control by Mann-Whitney test (FIGS. 4C, 4E, 4F), or Kruskal-Wallis test (FIG. 4G), ns, not significantly different.

FIG. 5A shows $Ca^{2+}$ response of Fluo-4 loaded Ocy454 cells treated with combination of parthenolide (PTL) and Taxol and subjected to 4 dynes/$cm^2$ FSS. Trace indicates average Fluo-4 fluorescence changes over time (>200 cells per treatment, n=3 independent experiments), % Cells Responding indicates number of cells with >25% increase in fluorescence, Peak(ΔF/F) indicates peak magnitude of $Ca^{2+}$ response. FIG. 5B shows control Ocy454 cells or cells treated with combination of PTL and Taxol subjected to fluid shear stress and immunoblotted for indicated proteins. Sclerostin to GAPDH and p-CaMKII to total-CaMKII ratios are shown (n=3 independent experiments). FIG. 5C shows control Ocy454 cells or Ocy454 cells treated with a combination of Taxol and PTL were immunostained for α-tubulin (red), Glu-tubulin (green), and DAPI (blue). Scale bar, 10 μm. n=4 independent experiments. Graphs depict mean±sem.  p<0.001, * p<0.0001 versus control by two tailed Mann-Whitney test (FIG. 4A) or Kruskal-Wallis test (FIG. 4B), ns, not significantly different. FIG. 5D shows atomic force microscopy nano-indentation of control Ocy454 cells or cells treated with Taxol, parthenolide (PTL), and a combination of PTL and Taxol. Box edges denote $25^{th}$ and $75^{th}$ percentiles, whiskers denote $10^{th}$ and $90^{th}$ percentiles, and white line indicates mean. Data are from 3 independent experiments with number of cells per group indicated. FIG. 5E shows protein extracts from control Ocy454 cells or Ocy454 cells treated with PTL, Taxol or combination of PTL and Taxol were probed for Glu-tubulin and α-tubulin. The Glu-tubulin to α-tubulin ratio (mean±sem) is shown. For FIGS. 5D-5E statistical significance was determined using one-way ANOVA with Holm-Sidak's multiple comparison test. *denotes statistical significance between all groups.

FIG. 6A shows Ocy454 cells and sections of murine long bones immunostained with α-tubulin (red), TRPV4 (green), and DAPI (blue). Scale bar, 100 μm. n=3 independent experiments, n=3 mice. FIG. 6B shows immunoblotting of Ocy454 whole cell lysates and murine long bone extracts for TRPV4 and GAPDH. n=3 independent experiments. FIGS. 6C-6D show $Ca^{2+}$ response of Ocy454 cells in the presence or absence (control) of the TRPV4 antagonist GSK-2193874 (FIG. 6C) or transfected with control or TRPV4 siRNA (FIG. 6D) and subjected to 4 dynes/$cm^2$ FSS. Trace indicates average Fluo-4 fluorescence changes over time (>200 cells per treatment, n=3 independent experiments), % Cells Responding indicates number of cells with >25% increase in fluorescence, Peak(ΔF/F) indicates peak magnitude of $Ca^{2+}$ response. FIG. 6E shows Ocy454 cells treated with or without (control) TRPV4 antagonist (GSK-2193874) subjected to 4 dynes/$cm^2$ FSS and immunoblotted for the indicated proteins. Sclerostin to GAPDH and p-CaMKII to total-CaMKII ratios are shown (n=3 independent experiments). FIG. 6F shows Ocy454 cells transfected with control or TRPV4 siRNA subjected to 4 dynes/$cm^2$ FSS and immunoblotted for the indicated proteins. Sclerostin to GAPDH, p-CaMKII to total-CaMKII, and TRPV4 to GAPDH ratios are shown (n=3 independent experiments). Image is from a single exposure of a contiguous membrane. Dotted lines indicate the removal of irrelevant lanes. FIG. 6G shows Ocy454 cells treated with or without (control) the TRPV4 agonist GSK-1016790A and immunoblotted for indicated proteins. Sclerostin to GAPDH and p-CaMKII to total-CaMKII ratios are shown (n=3 independent experiments). Graphs depict mean±sem. * p<0.05,  p<0.001, *p<0.0001 versus control by two tailed Mann-Whitney test (FIG. 6C, 6D, 6G), or Kruskal-Wallis test (FIG. 6E, 6F). ns, not significantly different.

FIG. 7A shows $Ca^{2+}$ response Ocy454 cells treated with α-N-acetyl cysteine (NAC) and subjected to 4 dynes/$cm^2$ fluid shear stress. Trace indicates average Fluo-4 fluorescence changes over time (>200 cells per treatment, n=3 independent experiments), % Cells Responding indicates number of cells with >25% increase in fluorescence, Peak(ΔF/F) indicates peak magnitude of $Ca^{2+}$ response. The $Ca^{2+}$ data for the control at 4 dynes/$cm^2$ fluid shear stress is the same trace as in FIG. 1B, as these controls were run in parallel with the NAC interventions. FIG. 7B shows Ocy454 cells treated with or without (control) NAC were subjected to fluid shear stress and immunoblotted for indicated proteins. Sclerostin to GAPDH and p-CaMKII to total-CaMKII ratios are shown (n=3 independent experiments). FIG. 7C shows Ocy454 cells treated with $H_2O_2$ and immunoblotted for the indicated proteins. Sclerostin to GAPDH and p-CaMKII to total-CaMKII ratios are shown (n=3 independent experiments). Graphs depict mean±sem. *p<0.0001 versus control by two tailed Mann-Whitney test (FIGS. 7A, 7C) or Kruskal-Wallis test (FIG. 7B) ns, not significantly different. FIG. 7D shows $Ca^{2+}$ and ROS response in Ocy454 cells simultaneously loaded with Fluo-4 $Ca^{2+}$ indicator and CellROX ROS indicator and subjected to 4 dynes/$cm^2$ fluid shear stress. $Ca^{2+}$ and ROS traces are aggregated from >200 cells per treatment over n=3 independent experiments. Graphs depict mean±sem. Statistical significance was determined using one-way ANOVA with Holm-Sidak's multiple comparison test. p<0.001, ***p<0.0001 versus control, underline depicts statistical significance between indicated groups. ns, not significantly different.

FIG. 8A shows immunoblotting of Ocy454 whole cell lysates for NOX2 and α-tubulin. FIG. 8B shows ROS response in Ocy454 cells loaded with CellROX ROS indicator and subjected to 4 dynes/$cm^2$ fluid shear stress. ROS traces are aggregated data from >200 cells per treatment from n=3 independent experiments. Graphs depict mean±sem. Statistical significance was determined using one-way ANOVA with Holm-Sidak's multiple comparison test. *p<0.0001. FIG. 8C shows $Ca^{2+}$ response of Ocy454 cells treated with GP91ds-TAT and subjected to 4 dynes/$cm^2$ fluid shear stress. $Ca^{2+}$ traces are aggregated from >200 cells per treatment from n=3 independent experiments. The $Ca^{2+}$ data for the control at 4 dynes/$cm^2$ fluid shear stress is the same trace as in FIG. 5A, as these controls were run in parallel with the GP91ds-TAT interventions. FIG. 8D shows Ocy454 cells treated with or without (control) GP91ds-TAT subjected to fluid shear stress and immunoblotted for indicated proteins. Sclerostin to GAPDH and p-CaMKII to total-CaMKII ratios are shown (n=3 independent experiments). Graphs depict mean±sem. $^{}p<0.001$, $^{*}p<0.0001$ versus control by two tailed Mann-Whitney test (FIG. 8C) or Kruskal-Wallis test (FIG. 8D), ns, not significantly different. FIG. 8**E is a representation of MT-dependent mechanotransduction pathway showing the interventions used to alter osteocyte mechano-response (top). Proposed model of Glu-tubulin and cytoskeletal stiffness regulation of osteocyte response to mechanical stimuli (bottom), in which cytoskeletal stiffness tunes the mechano-responsive range of an osteocyte. This responsive range can be influenced not only by the cytoskeletal stiffness, but also by altering the amount of FSS applied to the cell.

DETAILED DESCRIPTION OF THE INVENTION

Figure 1A:
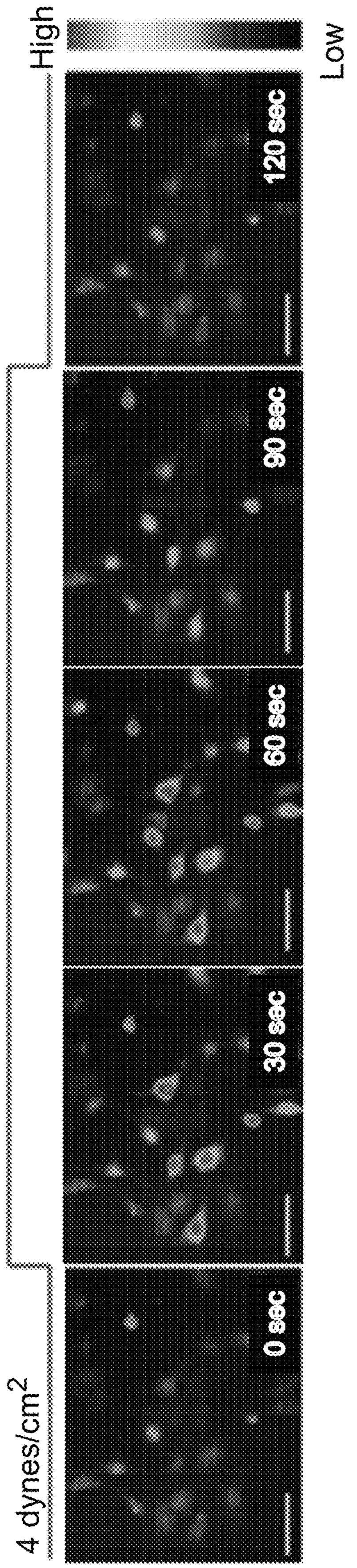
FIGS. 1A-1E show the fluid shear stress-induced $Ca^{2+}$ response is required for CaMKII phosphorylation and reduction in sclerostin.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise.

As used herein, "comprise" or "comprises" or "comprising", except where the context requires otherwise due to express language or necessary implication, are used in an inclusive sense, i.e. to specify the presence of the stated features but not to preclude the presence or addition of further features in various embodiments of the invention.

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "treating" or the phrase "treating a bone-related disorder" includes, but is not limited to, preserving bone mass, improving bone mass, delaying or stopping loss of bone, restoring mechano-signaling, altering or improving microtubule dependent cytoskeletal stiffness via the administration of the drugs or therapeutic agents disclosed herein. Generally, in treating a bone-related disorder in a subject a therapeutic or beneficial result is achieved, for example, an alleviation of symptoms, a remission or other improvement.

As used herein, the terms "effective amount" or "pharmacologically effective amount" are interchangeable and refer to an amount that results in an improvement or remediation of the symptoms of the bone-related disorder. Those of skill in the art understand that the effective amount or pharmacologically effective amount may improve the patient's or subject's condition, but may not be a complete cure of the disease and/or condition.

As used herein, the term "subject" refers to any target or recipient of the treatment.

In one embodiment of the present invention there is provided a method for treating a bone-related disorder in a subject, the method comprising administering to the subject an amount of at least one of a microtubule altering drug, a TRPV4 agonist, or a NOX2 activator pharmacologically effective to treat the bone-related disorder. Further to this embodiment, the method may comprise administering to the subject at least one of an anti-sclerostin agent, a parathyroid hormone agonist, a bisphosphonate, an estrogen mimic, or a selective estrogen receptor modulator. In this further embodiment the anti-sclerostin agent may be a monoclonal antibody or a fragment thereof. Representative examples of the anti-sclerostin agent are romosozumab or blosozumab.

In both embodiments, the microtubule altering drug may be a microtubule disrupting drug or a microtubule stabilizing drug. Examples of the microtubule disrupting drug are selected from the group consisting of Nocodazole, Colchicine, LC1/Parthenolide, Costunolide, Tubacin, 2-phenyl-4-quinolone, Polygamain, Azaindole, a Vinca alkaloid, and Colcemid. Examples of the microtuble stabilizing drug are a taxane or eothinolone. In both embodiments, representative examples of the TRPV4 agonist include but are not limited to GSK1016790A or RN-1747.

In addition, the bone-related disorder may be selected from the group consisting of achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthes' Disease, adolescent idiopathic scoliosis, infantile onset multi-system inflammatory disease, Winchester Syndrome, Menkes Disease, Wilson's Disease, ischemic bone disease, Legg-Calve-Perthes disease, regional migratory osteoporosis, anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy associated bone loss, tumor induced bone loss, cancer-related bone loss, hormone ablative bone loss, multiple myeloma, drug-induced bone loss, anorexia nervosa, disease associated facial bone loss, disease associated cranial bone loss, disease associated boneloss of the jaw, disease associated bone loss of the skull, bone loss associated with aging, facial bone loss associated with aging, cranial bone loss associated with aging, jaw bone loss associated with aging, skull bone loss associated with aging, and bone loss associated with space travel.

In another embodiment of the present invention, there is provided a method for treating a bone-related disorder in a subject, the method comprising administering to the subject one or more times an amount of a microtubule disrupting drug pharmacologically effective to treat the bone-related disorder. Further to this embodiment, the method may comprise administering to the subject at least one of a microtubule stabilizing drug, a TRPV4 agonist, a NOX2 activator, an anti-sclerostin agent, a parathyroid hormone agonist, a bisphosphonate, an estrogen mimic, or a selective estrogen receptor modulator. In both embodiments, the microtuble disrupting drug, the microtubule stabilizing drug, the TRPV4 agonist, the anti-sclerostin agent, and the bone-related disorders are as described supra.

In yet another embodiment of the present invention, there is provided a method for treating a bone-related disorder in a subject, the method comprising administering to the subject one or more times an amount of a microtubule stabilizing drug pharmacologically effective to treat the bone-related disorder. Further to this embodiment, the method may comprise administering to the subject at least one of a microtubule disrupting drug, a TRPV4 agonist, a NOX2 activator, an anti-sclerostin agent, a parathyroid hormone agonist, a bisphosphonate, an estrogen mimic, or a selective estrogen receptor modulator. In both embodiments, the microtuble stabilizing drug, the microtuble disrupting drug, the TRPV4 agonist, the anti-sclerostin agent, and the bone-related disorders are as described supra.

In yet another embodiment of the present invention, there is provided a method for treating a bone-related disorder in a subject, the method comprising administering to the subject one or more times an amount of a TRPV4 agonist pharmacologically effective to treat the bone-related disorder. Further to this embodiment the method may comprise administering to the subject at least one of a microtubule altering drug, a NOX2 activator, an anti-sclerostin agent, a parathyroid hormone agonist, a bisphosphonate, an estrogen mimic, or a selective estrogen receptor modulator. In both embodiments, the microtuble altering drug, the anti-sclerostin agent, and the bone-related disorders are as described supra.

In yet another embodiment of the present invention, there is provided a method for treating a bone-related disorder in a subject, the method comprising administering to the subject one or more times an amount of a NOX2 activator pharmacologically effective to treat the bone-related disorder. Further to this embodiment, the method may comprise administering to the subject at least one of a microtubule altering drug, a TRPV4 agonist, an anti-sclerostin agent, a parathyroid hormone agonist, a bisphosphonate, an estrogen mimic, or a selective estrogen receptor modulator. In both embodiments, the microtubule altering drug, a TRPV4 agonist, an anti-sclerostin agent, and the bone-related disorders are as described supra.

In yet another embodiment of the present invention, there is provided a method for treating a bone-related disorder in a subject, comprising administering to the subject an amount of a microtubule altering drug pharmacologically effective to treat the bone-related disorder. In a further embodiment, the method comprises administering to the subject at least one of an anti-sclerostin agent, a parathyroid hormone agonist, a bisphosphonate, an estrogen mimic, or a selective estrogen receptor modulator each of which may be as described supra.

In both embodiments, the microtubule altering drug may be a microtubule disrupting drug or a microtubule stabilizing drug as described supra. In both embodiments, the bone-related disorder may be selected from the group consisting of those disorders as described supra.

In yet another embodiment of the present invention, there is provided a method for treating a bone-related disorder in a subject, comprising administering to the subject one or more times an amount of a microtubule disrupting drug, an amount of a microtubule stabilizing drug or a combination thereof, each pharmacologically effective to treat the bone-related disorder. In this embodiment, the microtubule disrupting drug and the microtubule stabilizing drug may be as described supra. In this embodiment the bone-related disorder may be osteoporosis or a disorder associated therewith.

In yet another embodiment of the present invention, there is provided a method for increasing bone mass in a subject in need thereof, the method comprising administering to the subject one or more times an amount of a microtubule disrupting drug pharmacologically effective to decrease sclerostin in the subject. Further to this embodiment the method comprises administering to the subject at least once a microtubule stabilizing drug or an anti-sclerostin agent or a combination thereof.

In both embodiments, the microtubule disrupting drug may be as described supra. Particularly the microtubule disrupting drug is colchicine. In one aspect of the further embodiment, the microtubule stabilizing drug may be a taxane or eothinolone. In another aspect, the anti-sclerostin agent may be a monoclonal antibody or a fragment thereof. Particularly, the anti-sclerostin agent may be romosozumab or blosozumab. In both embodiments and aspects thereof the bone-related disorder may be osteoporosis or a disorder associated therewith.

Provided herein are methods and agents for improving the mechano-sensitivity of osteocytes to improve or maintain bone quality by tuning the microtubule network/cytoskeletal stiffness into a mechano-responsive range. These methods and agents are pharmacological interventions that alter microtubule dependent cytoskeletal (CSK) stiffness and/or its downstream signaling pathway in the osteocyte to ultimately control the bioavailability of sclerostin and other bone regulatory factors to regulate bone quality.

Microtubule altering drugs may be used alone or in combination with TRPV4 agonists and/or NOX2 activators to: (1) restore mechanical sensitivity in aged or "adapted bone" and (2) to enhance and mimic the mechano-response. A triple therapy of microtubule altering drugs, TRPV4 agonists and NOX2 activators may also be administered. Double or triple therapies comprising drug combinations of microtubule altering drugs, TRPV4 agonists and NOX2 activators may permit lower doses of each drug with less concomitant side effects and/or may enhance the effectiveness of either drug alone. Any of these single or combination therapies may be used in further combination with anti-sclerostin drugs or sclerostin targeting drugs to: (1) restore mechanical sensitivity in aged or “adapted bone” and (2) to enhance and mimic the mechano-response.

The present invention demonstrates that microtubule altering or targeting agents, for example, microtubule disrupting agents and microtubule stabilizing agents, and/or TRPV4 agonists and NOX2 activators are useful to improve the mechano-sensitivity of bone cells, such as osteocytes, to improve or to maintain bone quality by tuning the microtubule network/cytoskeletal stiffness into a mechano-responsive range. Further, these drugs may be combined with existing drugs, such as anti-sclerostin antibodies, for example, romosozumab or blosozumab, or Prolia, teriparatide (Forteo), abolparatide and/or bisphosphonates, to synergistically improve their action on bone. Generally, these drugs are taxanes, including paclitaxel and docetaxel, epithinolones, lauliamindes, Colchicine binding site inhibitors (CBSIs), colchicine, ZD6126, Combretastatins, nocodozole, 2-phenyl-4-quinolone, polygamain, azaindole, vinca alkaloids, including vinblastine, vincristine, and vinorelbine; and colcemid; Detyrosination inhibitors, like parthenolide, dimethylaminoparthenolide, Costunolide, or their pharmaceutical salts.

The therapeutic treatments and methods of applying the same generally realize a therapeutic effect against a bone-related disorder or disease or other related condition arising from a natural condition such as pregnancy or aging or as a result of a surgical procedure, such as a joint replacement. Representative examples of bone-related disorders are as described supra. In addition the therapies described herein are useful to sensitize mechano-responses for applications occurring during space flight or prolonged disuse such as from an extended stay in space. Particularly, the therapeutic targeting of microtubules in the skeleton and other tissues with colchicine may be useful against aging related changes in muscle, bone and white adipose tissue to decrease frailty and restore quality of life in the elderly.

In a non-limiting example, the present invention relates to a method for treating osteoporosis or other clinical conditions characterized by low bone mass or skeletal fragility in a subject. A therapeutic agent or agents that target the mechanotransduction pathways in osteocytes via the microtubules are administered. For example, taxanes, epithinolones, lauliamindes, colchicine binding site inhibitors (CBSIs), colchicine, ZD6126, combretastatins, nocodozole, 2-phenyl-4-quinolone, polygamain, azaindole, vinca alkaloids, vinblastine, vincristine, vinorelbine, colcemid, and detyrosination inhibitors or their pharmaceutical salts my be administered to the subject. More particularly, ZD6126, combretastatins (CA-4), AVE8062, Phenastatin, Podophyllotoxin, Steganacin, Nocodazole, Curacin A, 2-Methosyestradiol, ABT-751, T138067, BNC-105P, Indibulin, EPC2407, MPI-0441138, MPC-6827, CYT997, MN-029, CI-980, CP248, CP461, and TN16 or the pharmaceutical salts of any of these agents may be administered. Also the microtubule targeting agent may be an antimotic drug which exhibit diverse binding sites and their associated analogues as listed in Table 1.

TABLE 1

Antimitotic drugs, their diverse binding sites on tubulin and their stages of clinical development

| Binding Domain | Related drugs or Analogues | Therapeutic uses | Stage of clinical development |
|---|---|---|---|
| *Vinca* domain | Vinblastine (Velban) | Hodgkin’s disease, testicular germ-cell cancer | In clinical use, 22 combination trials in progress |
| | Vincristin (Oncovin) | Leukaemia, lymphomas | In clinical use, 108 combination trials in progress |
| | Vinorelbine (Navelbine) | Solid tumors, lymphomas, lung cancer | In clinical, 29 Phase I-III single & combination trials in progress |
| | Cryptophycin 52 | Solid tumors | Phase II finished |
| | Halichondrins, e.g., E7389 | | Phase I |
| | Dolastatins, e.g., TZ %-1027 | Potential vascular-targeting agent | Phase I, Phase II completed |
| | Hemiasterlins, e.g., HTI-286 | | Phase I |
| Colchicine domain | Colchicine | Non-neoplastic diseases (gout, familial Mediterranean fever | |
| | Combretastatins (AVE80621, CA-1-P, CA-4-P, N-acetyl-cholchincinol-O-phosphate, ZD6126) | Potential vascular-targeting agent | Phase I, II |
| | 2-Methoxyestradiol | | Phase I |
| | Methoxybenzene-sulphonamide (ABT-751, E7010) | Solid tumors | Phase I, II |
| Taxane site | Paclitaxel (Taxol), TL00139 and other analogs) | Ovarian, breast and lung tumors, Kaposi’s sarcoma, trials with numerous other tumors | In clinical use, 207 Phase I-III trials in the US; TL00139 is in Phase I trials |
| | Docetaxel (Taxotere) | Prostate, brain and lung tumors | 8 trials in the US, Phases I-III |

TABLE 1-continued

| Antimitotic drugs, their diverse binding sites on tubulin and their stages of clinical development | | | |
|---|---|---|---|
| Binding Domain | Related drugs or Analogues | Therapeutic uses | Stage of clinical development |
| | Epothilones (BMS-247550, epothilones B and D) | Paclitaxel-resistant tumors | Phases I-III |
| | Discodermolide | | Phase I |
| Other microtubule binding sites | Estramustine | Prostate | Phases I-III, in combinations with taxanes, epothilones and *Vinca* alkaloids |

See the National Institutes of Health Clinical Trials web site (www.clinicaltrials.gov), the European Organisation for Research and Treatment of Cancer web site (www.eortc.be) and the Proceedings of the American Association for Cancer Research meeting in 2003 (www.aacr.org); CA-4-P, combrestatin-A-4 3-O-phosphate; CA-1-P, combrestatin A-1-phosphate.

Moreover, any of these therapeutic treatments may be combined with an anti-sclerostin antibody such as Romosozumab, or with Prolia or a bisphosphonate, including but not limited to, Actonel, Binosto, Boniva, Reclast and Fosamax, an estrogen mimetic including but not limited to Evista, or with a synthetic form of parathyroid hormone such as Forteo or abolparatide (Tymlos). Furthermore, a therapeutic treament may comprise an antimitotic agent which binds tubulin as indicated in Table 1 in combination with another agent selected from the group consisting of Actonel, Binosto, Binova, Reclast, Evista, Forteo, Prolia, Romosozumab and Vitamin D.

In a related aspect, a therapeutic treatment stabilizes microtubles. A microtubule stabilizing drug includes, but is not limited to, paclitaxel or epothilone D (BMS-241027). In a further related aspect, a therapeutic treatment activates TRP channel activation in the cell surface membrane. A TRP $Ca^{2+}$ channel agonist includes, but is not limited to, GSK1016790A or RN-1747 and analogs or derivatives thereof, or a pharmaceutical salt thereof.

The dosage of each treatment depends on the type of drug(s) or agent(s) being administered, whether the drug or agent is used in an individual having a bone disorder or in a healthy individual, the severity of the disorder or other condition(s) of the patient. In consideration of the teachings provided herein, one having ordinary skill in the art is well able to determine an effective dosage for a patient suffering from a bone disorder. As such, treatment intervals will depend on the particular dosage determined for the patient. Treatment may be administered multiple times per day, daily, or less frequently.

For example, a microtubule disrupting drug may be administered in a range from about 0.01 micrograms/kg to about 100 micrograms/kg. In a nonlimiting example, colchicine would likely be administered in an amount of about 5 micrograms/kg to about 20 micrograms/kg of the subject's body weight. The administration of parthenolide as LC-1 (Parthenolide pro-drug) or as Feverfew extract may be from about 0.1-4.0 mg day total. A microtubule stabilizing drug such as epothilone D may be administered in a range from about 1 to 30 micrograms/kg of the subject's body weight. TRPV4 agonists may be administered to an effective serum concentration of 1-50 nM.

The following examples are given for the purpose of illustrating various embodiments of the invention and are not meant to limit the present invention in any fashion.

Example 1

Materials and Methods

Chemicals and Reagents

Taxol, colchicine, GSK2193874, GSK-1016790A, N-acetylcysteine, and parthenolide were purchased from Sigma. BAPTA AM ester was from Cayman Chemical. GP91ds-TAT was from Anaspec. SiR-tubulin was from Cytoskeleton, Inc. CellROX Deep Red Reagent and Fluo-4AM ester were purchased from ThermoFisher.

Cell Culture and Treatments

Osteocyte-like Ocy454 cells (provided by Dr. Divieti-Pajevic, Boston University) were cultured on type I rat tail collagen (BD Biosciences) coated dishes in α-MEM supplemented with 5% FBS. Cells were maintained at 33° C. and 5% $CO_2$. Prior to experiments cells were seeded into a tissue culture treated vessel and maintained at 37° C. and 5% $CO_2$ overnight. For alteration of the MT network, cells were pretreated with 0.1% DMSO (control), colchicine (2 mM, 20 min), Taxol (1 mM, 2 h), or PTL (25 mM, 2 h). In the case of the combined treatment, cells were dosed with PTL for 30 min before Taxol was added to the same media for an additional 1.5 h for a total incubation time of 2 h. To modulate TRPV4 activity, the cells were treated with the TRPV4 antagonist GSK2193874 (15 mM, 30 min) or TRPV4 agonist GSK-1016790A (15 mM, 30 min) prior to the stimulation of the cells. To modulate reactive oxygen species, the cells were treated with NAC (10 mM, 15 min), $H_2O_2$(100 mM, 30 min), or gp91ds-TAT (10 mM, 30 min) prior to the stimulation of the cells.

Transient Transfections

Ocy454 cells were transfected with JetPrime reagent (Polypus), as previously described (62). ON-TARGETpIus mouse TRPV4 siRNA and ON-TARGETpIus non-targeting siRNA were purchased from Dharmacon. siRNAs were used at 0.42 μg/$cm^2$. Cell exposure to FSS was begun 48 h post-transfection.

Fluid Flow

Cells in culture were exposed to fluid flow using a custom FSS device (63). Cell media was removed and cells were rinsed in HEPES-buffered Ringer solution containing 140 mM NaCl, 4 mM KCl, 1 mM $MgSO_4$, 5 mM $NaHCO_3$, 10 mM glucose, 1.8 mM $CaCl_2$ and 10 mM HEPES (pH 7.3). Ringer solution was also used as fluid flow buffer. For Calcium-free conditions, HEPES-buffered Manganese Ringer solution, containing 140 mM NaCl, 4 mM KCl, 1 mM $MgSO_4$, 5 mM $NaHCO_3$, 10 mM glucose, 2 mM MnCl and 10 mM HEPES (pH 7.3), was used, and cells were loaded with BATPA AM ester (10 μM, 30 min).

Calcium and ROS Imaging

Cells were seeded into optically clear 96-well plates (Corning), incubated overnight at 37° C., and 5% $CO_2$ and treated as indicated. For $Ca^{2+}$ imaging, cells were loaded with Fluo-4 AM ester (ThermoFisher, 5 μM) for 30 min, washed, and allowed to rest for 15 min to allow dye de-esterification, as described. For ROS imaging, cells were loaded with CellROX (ThermoFisher, 5 μM) for 30 min and then washed 3 times, per the manufacturer's recommendations. Individual wells were imaged as described (39). Time-lapse fluorescence intensity measurements were collected using ImageJ Time Series Analyzer plugin and data was analyzed and plotted using Origin Pro software. Final results represent a minimum of three independent experiments performed on separate days with new cultures (n>700 cells/treatment group). All conditions were run with controls on each experimental day.

Atomic Force Microscopy

Ocy454 cells were plated onto 22 mm×22 mm glass coverslips and allowed to grow for 16-24 h at 37° C., 5% $CO_2$ with αMEM media. Thereafter, cells were washed with PBS before being incubated with pharmacological agents as indicated for 2 h at 37° C., 5% $CO_2$ in αMEM. After each treatment, cells were transferred to 60 mm culture dishes with pre-warmed HEPES based media containing identical concentrations of the aforementioned agents. Cells were probed with an MFP-1D atomic force microscope (Asylum Research) using MLCT cantilevers (Bruker) with a nominal spring constant of k=0.01 N/m. The pull distance used was 2 μm with a tip velocity of 4 μm/s to generate ~1-2 nN of force onto the cell corresponding to ~1 μm indentation ensuring that the cytoskeleton was effectively being probed. The elastic moduli (stiffness) of the cells were calculated using the Sneddon Hertz model as described (66).

Immunofluorescence

Ocy454 cells seeded and grown on glass cover slips were fixed and permeabilized as described (67). For histological sections of bone, decalcified, paraffin embedded sections were processed as described. Cover slips were incubated in SuperBlock PBS (Life Technologies) for 1 h before the addition of primary antibodies. Primary antibodies were diluted in SuperBlock PBS and added to the coverslips for an overnight incubation at 4° C. Secondary antibodies were diluted in SuperBlock PBS and incubated at room temperature for 6 h. Coverslips were mounted using ProLong Diamond with DAPI (Life Technologies). The antibodies used were: a-tubulin (Sigma, T9026), Glu-tubulin (Abcam, ab48389) and TRPV4 (Abcam, ab39260). Goat anti-mouse Alexa 488, 647 and goat anti-rabbit Alexa 488, 568 were purchased from Life Technologies. Actin was stained using phalloidin-TRITC (Molecular Probes). Slides were imaged as described (69).

SiR-Tubulin Labeling and Confocal Imaging

Murine long bones (tibia, fibula) were isolated, flushed of marrow, and placed in 60 mm Fluo-dish glass bottom plates. These long bones were then incubated in αMEM containing the live cell tubulin stain, SiR-tubulin (1 uM; 37° C. and 5% $CO_2$ for 2 h). Confocal fluorescent imaging (Nikon A1R; 40× H2O Obj, 1,4NA) was used to profile the structure of the MT network in the bone embedded osteocytes as previously described.

Western Blotting

Western blotting of whole cell extracts isolated from cells in culture following FSS or extracts isolated from murine long bone were done. Equal amounts of protein were loaded and electrophoresed on 10% SDS-PAGE gels and transferred to polyvinylidene difluoride membranes. Membranes were blocked in 5% non-fat dry milk (unless otherwise stated), probed with the indicated primary antibodies overnight and 4° C. Antibodies were detected with the appropriate horseradish peroxidase-conjugated secondary antibodies (Cell Signaling Technology) and enhanced chemiluminescence detection reagent (Biorad). The antibodies used were: sclerostin (R&D Sytems, AF1589), α-tubulin (Sigma, T9026), Glu-tubulin (Abcam, ab48389), phospho-CamK II $Thr^{286}$ (Cell Signaling Technologies, 12716S), total CaMKII (Cell Signaling Technologies, 11945S), and GAPDH (Millipore, MAB374). Blots were acquired using an EpiChem gel documentation system (UVP Bioimaging Systems) and analyzed using ImageJ software.

Quantitative RT-PCR

RNA extraction was done by Directzol RNA mini prep (Zymo). RNA was reverse transcribed with either iScript (BioRad) or RevertAid (Fermentas) reverse transcription master mix, according to the manufacturer directions. Quantitative real time PCR was carried out by SYBR green master mix from Quanta using an Applied Biosystems 7300 sequence detection system. A melting curve was performed to ensure amplification of a single PCR product. For each sample, the relative gene expression was determined by simultaneously normalizing the gene of interest with three housekeeping genes (Rpl13, Hprt and Gapdh) by the $2^{-\Delta\Delta Ct}$ method, using GeNorm v3.5 software (Ghent University Hospital Ghent, Belgium). Primer sequences are available upon request.

Statistical Analysis

Experiments were repeated a minimum of 3 times with triplicate samples, unless indicated otherwise. Graphs show averages with error bars indicating standard error. Data normality was assessed by GraphPad Prism 6 software by D'Agostino-Pearson omnibus normality test. For normally distributed data, samples were compared by an ANOVA for unpaired samples with a Holm-Sidak post-hoc test, as appropriate, using GraphPad Prism 6 software. For nonparametric data, a two tailed Mann-Whitney test or Kruskal-Wallis test was performed, as indicated. A p-value <0.05 was used as a threshold for statistical significance.

Example 2

Figure 1B:
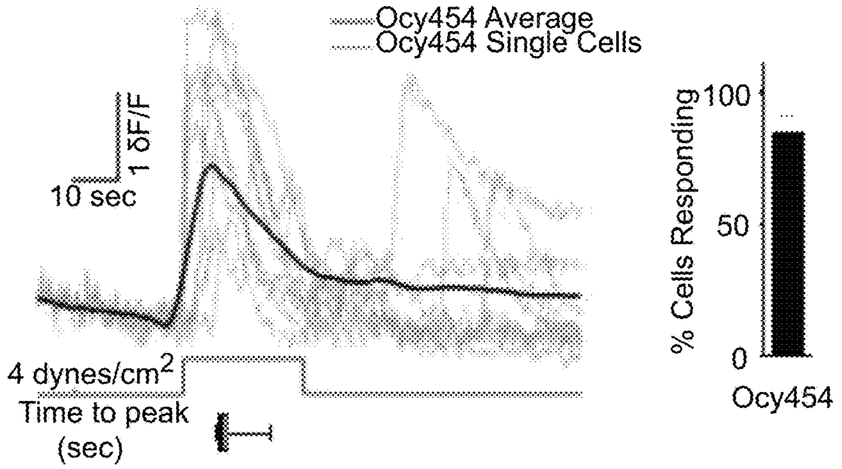
Figure 1C:
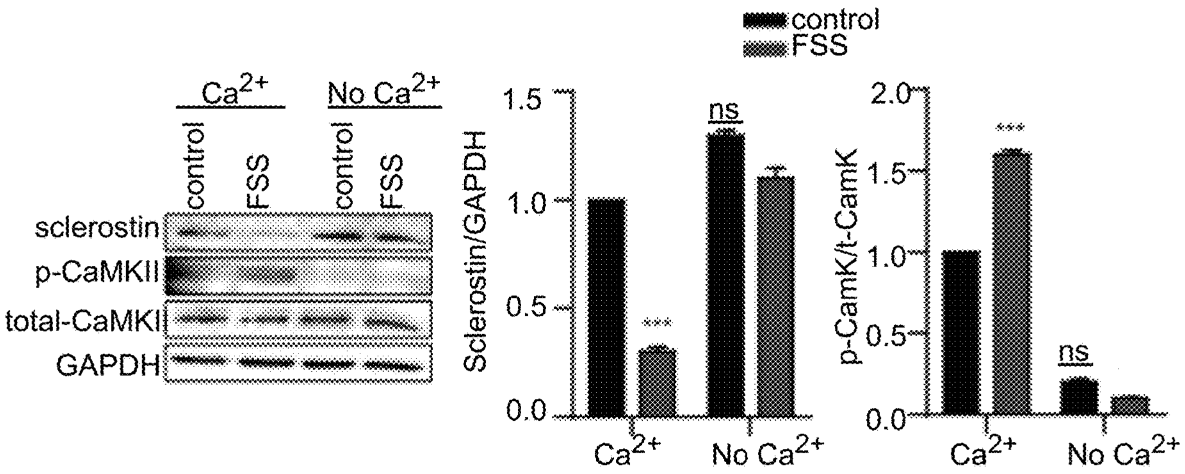

Ocy454 Cells Respond to FSS with a Rapid Increase in Intracellular $Ca^{2+}$ that is Required for CaMKII Phosphorylation and the Mechanically-Induced Decrease in Sclerostin Unlike some of the commonly used osteocyte cell lines, the Ocy454 osteocyte line, derived from the Immortomouse, reliably produces detectable sclerostin protein and is sensitive to mechanical stimuli (27). In Ocy454 cells loaded with the $Ca^{2+}$ indicator dye Fluo-4AM, fluid shear stress at 4 dynes/$cm^2$ elicited a rapid, transient increase in intracellular $Ca^{2+}$ concentration in ~84% of cells (FIGS. 1A-1B), resulting in activation of CaMKII and a concomitant 3-fold decrease in sclerostin protein observed within 5 minutes post-fluid shear stress (FIG. 1C). The fluid shear stress-induced CaMKII phosphorylation and decrease in sclerostin protein was inhibited when $Ca^{2+}$ signaling was blocked by loading the cells with BAPTA AM and removing $Ca^{2+}$ from the fluid flow buffer (FIG. 1C), demonstrating that $Ca^{2+}$ was required for CaMKII phosphorylation and the decrease in sclerostin. Inhibition of CaMKII signaling with KN-93

Figure 1D:
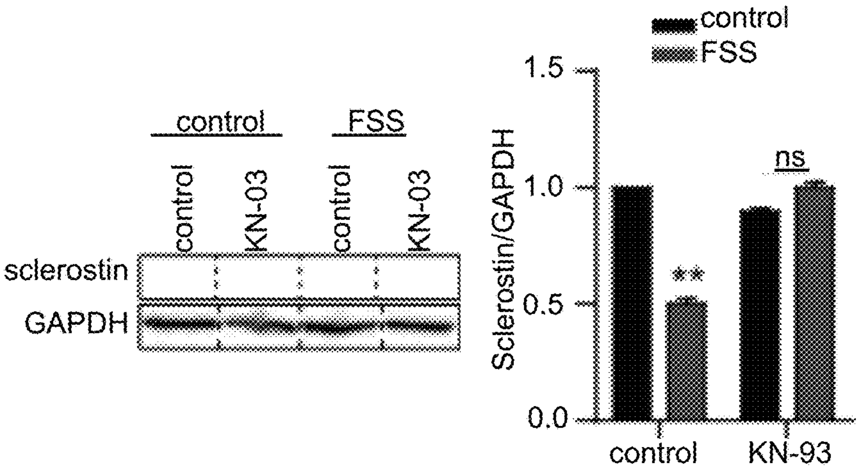
Figure 1E:
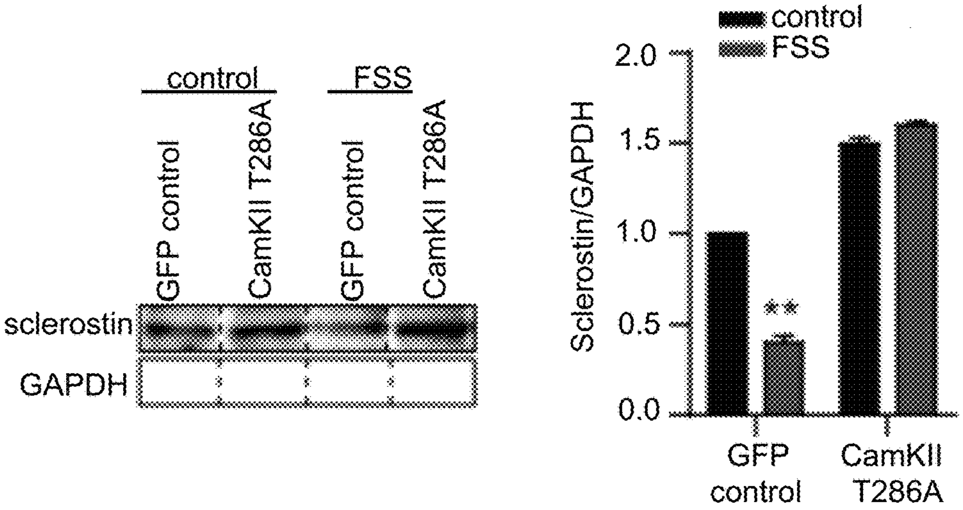

(FIG. 1D) or by overexpression of a dominant negative CaMKII (T286A) construct (FIG. 1E) prevented the FSS-induced sclerostin decrease.

Example 3

Figure 2A:
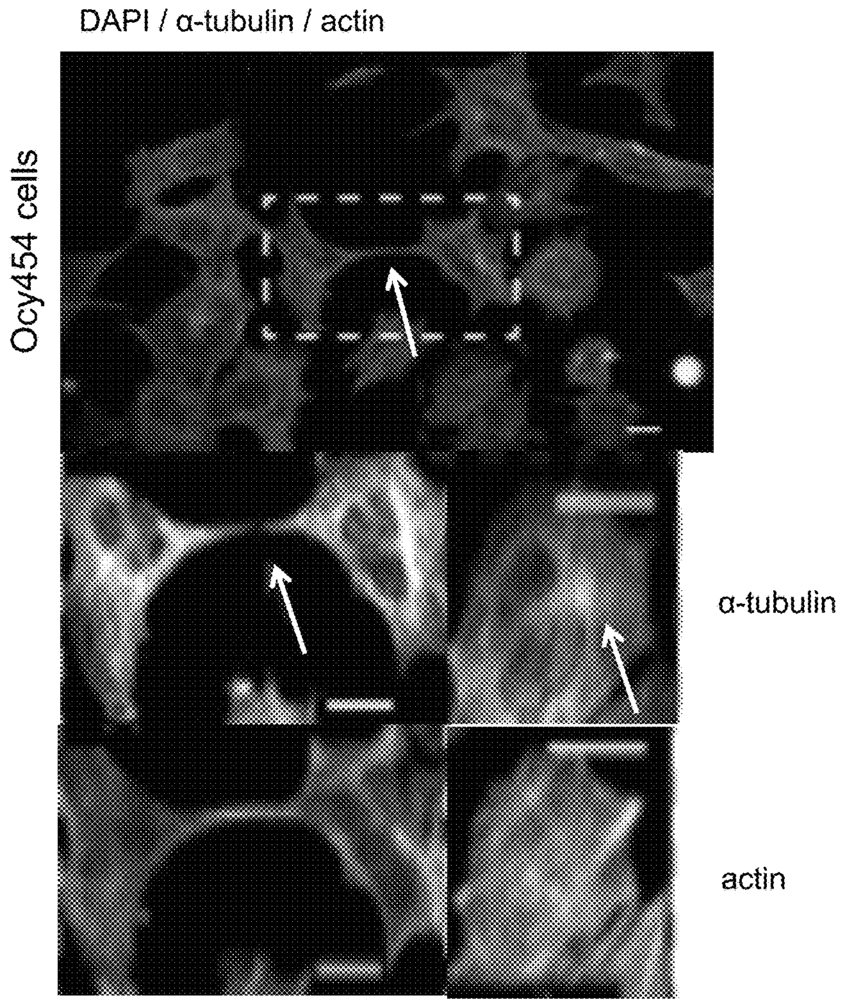
FIGS. 2A-2F show that an intact MT network is required for fluid shear stress-induced $Ca^{2+}$ influx, CaMKII phosphorylation, and decreased sclerostin abundance.
Figure 2B:
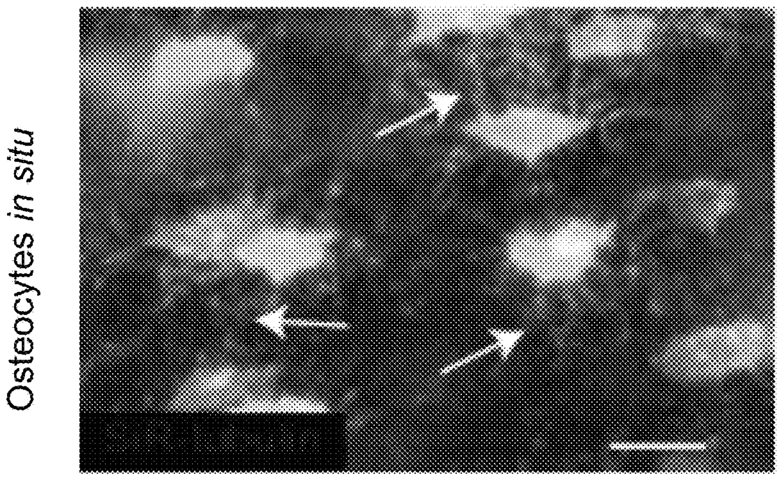

Microtubules are Present in the Putative Mechano-Sensitive Structures of Ocy454 Cells The cytoskeleton, comprised of actin, microtubules and intermediate filament networks, is a dynamic structural and signaling scaffold within all cells. A key function of the cytoskeleton is to transmit mechanical forces to proteins and enzymes that generate biological signals during mechanotransduction. In other cell types, microtubules have been implicated in mechanotransduction-elicited $Ca^{2+}$ signaling (28-30). In bone cells, an intact microtubule network is required for mechano-sensation by osteoblasts or osteocytes in culture (31-34), and the microtubule network of osteocytes remodels and reorients itself in response to FSS (34-36). Additionally, microtubules are an important component of the primary cilia, which has been proposed to be a mechano-sensor in osteocytes (16, 37). Another putative mechano-sensitive component is the long cellular process, extending from the cell body of the osteocyte, which is sensitive to FSS application (14). Immunofluorescent labeling of Ocy454 cells revealed abundant microtubules within the cell processes and primary cilia of Ocy454 cells (FIG. 2A). Similarly, the use of SiR-tubulin to label microtubules in murine femurs ex vivo, revealed distinct fluorescence within the osteocyte cell processes, indicating the presence of microtubules within the proposed mechano-sensitive structures of osteocytes (FIG. 2B).

Example 4

Microtubules are Required for the Osteocyte Response to FSS

Figure 2C:
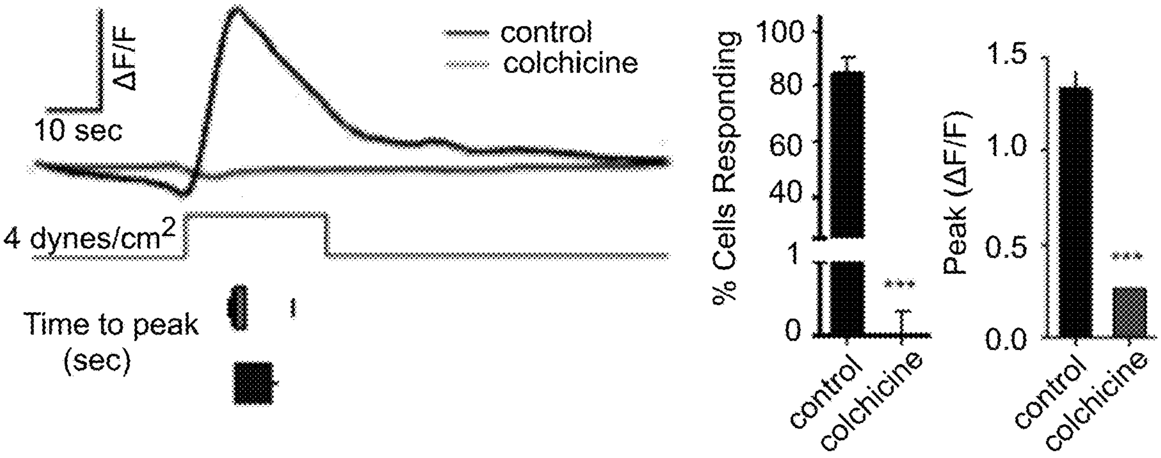
Figure 2D:
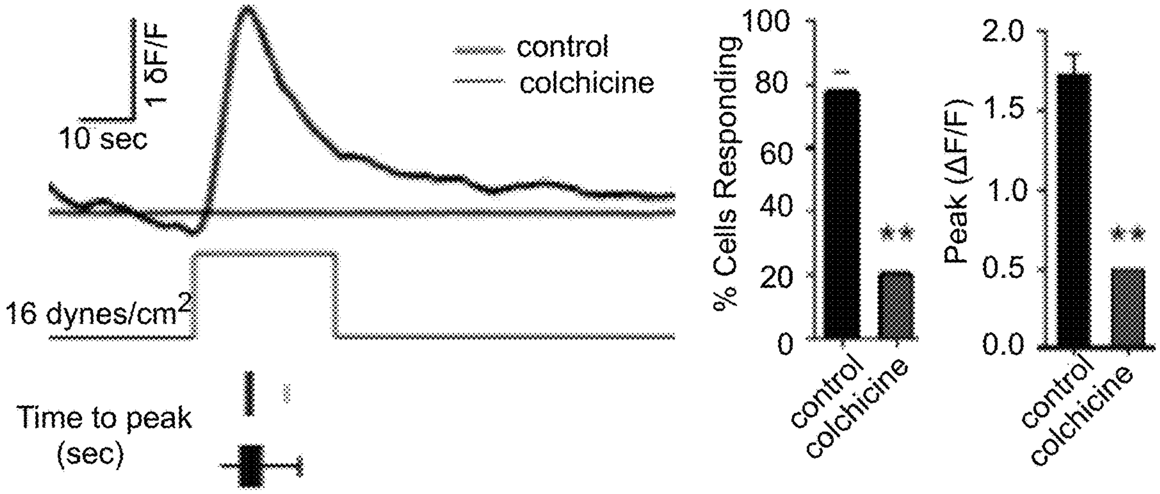
Figure 2E:
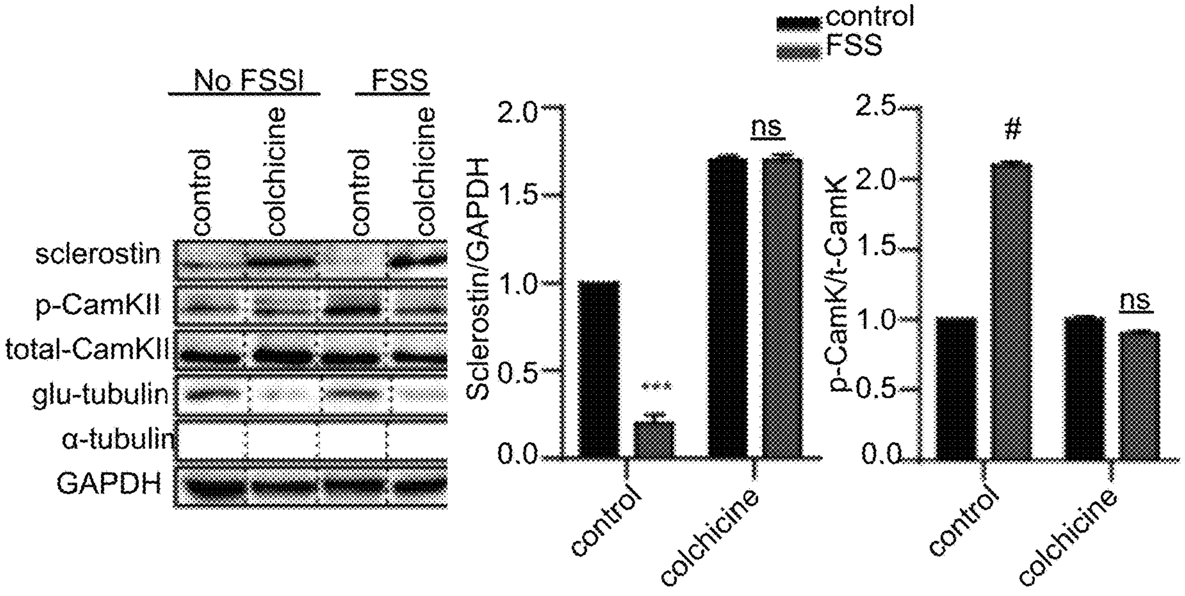
Figure 2F:
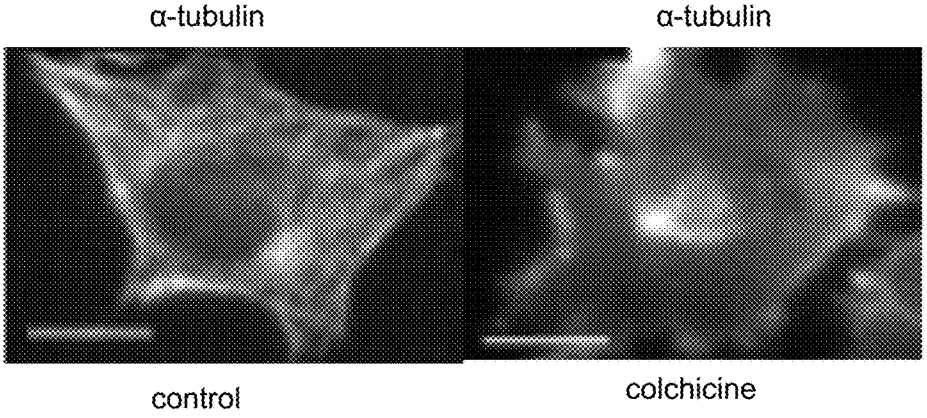

The microtubule network is dynamically unstable with microtubule-end binding proteins and post-translational modifications promoting microtubule filament disassembly or growth. Colchicine, a drug that binds tubulin and promotes microtubule depolymerization, inhibits ERK signaling, cell proliferation, and altered osteoblast gene expression (for genes encoding osteopontin, collagen, and matrix metalloproteinases) in osteoblasts and osteocytes exposed to mechanical cues (31-34). Consistent with these reports, there was a reduction of the microtubule network density in Ocy454 cells with colchicine reduced responses to fluid shear stress. In response to either 4 or 16 dynes/$cm^2$ of FSS, colchicine treatment decreased the number of cells responding (suggesting decreased mechano-sensitivity), while also reducing the magnitude (peak DF/F) of the $Ca^{2+}$ response (suggesting decreased mechano-responsiveness) in cells that did respond (FIGS. 2C-2D). Likewise, microtubule network disruption with colchicine eliminated the FSS-induced increase in CaMKII phosphorylation and decrease in sclerostin protein (FIG. 2E). Immunofluorescent labeling validated the disruption of microtubules following colchicine treatment (FIG. 2F). These data demonstrated that an intact microtubule network was required for mechanotransduction-elicited $Ca^{2+}$ influx, CaMKII phosphorylation, and decrease in sclerostin in osteocytes.

Example 5

Figure 3A:
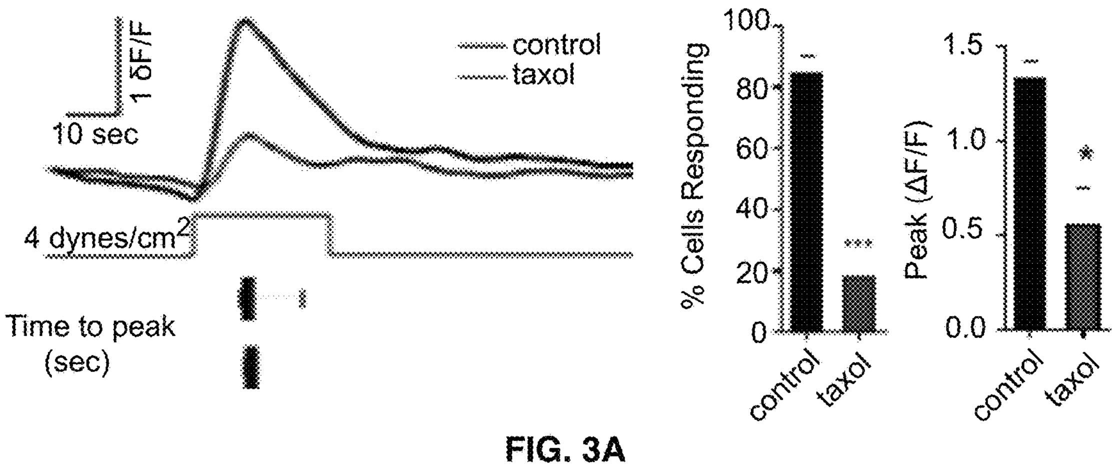
FIGS. 3A-3D show that Taxol blunts the fluid shear stress-induced $Ca^{2+}$ response, phosphorylation of CaMKII, and sclerostin decrease but is overcome by increased FSS.
Figure 3B:
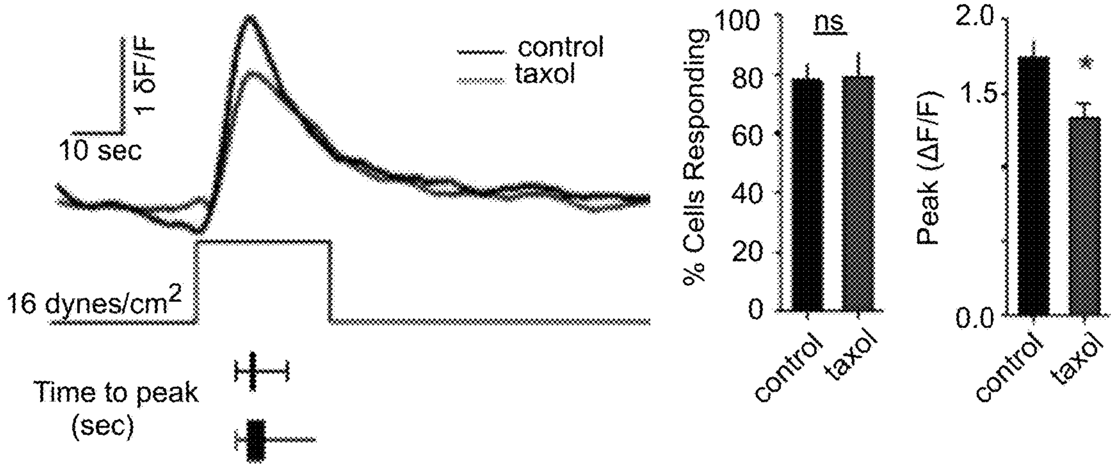
Figure 3C:
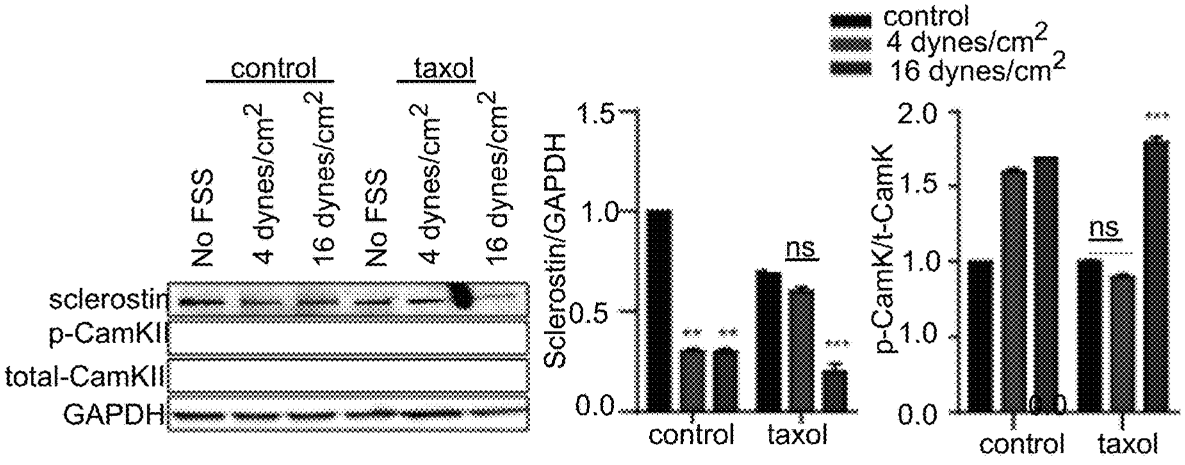
Figure 3D:
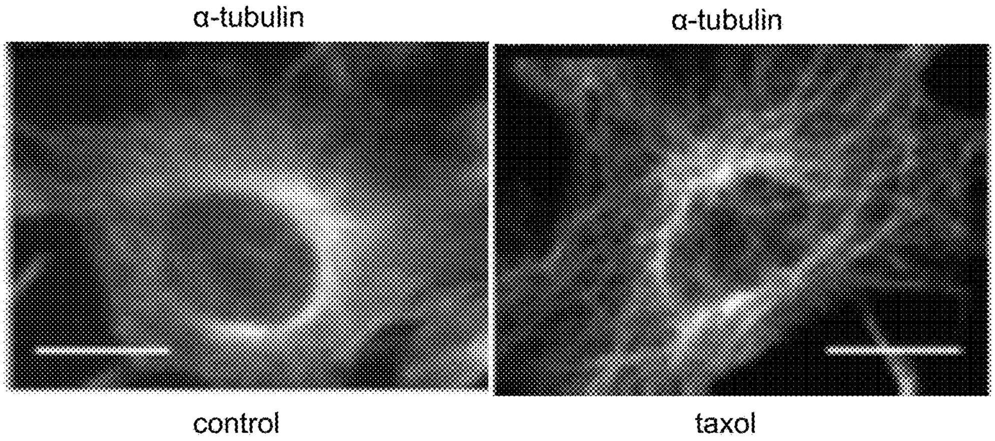

Microtubule Stabilization Alters the Set Point for FSS-Induced $Ca^{2+}$ Influx, CaMKII Activation, and Sclerostin Abundance The broad impact of the microtubule network on regulating osteocyte mechanotransduction was determined. The drug Taxol binds to and stabilizes the microtubule filament against depolymerization, thereby increasing microtubule network density. Real time $Ca^{2+}$ imaging of Ocy454 cells treated with Taxol showed a statistically significant decrease in the percentage of cells responding to 4 dynes/$cm^2$ FSS, as well as a decrease in the magnitude (peak DF/F) of their response (FIG. 3A). However, unlike the effect of colchicine-mediated microtubule depolymerization, the Taxol-induced suppression of both mechano-responsiveness and mechano-sensitivity was restored at 16 dynes/$cm^2$ FSS (FIG. 3B). Consistent with the impact of increased microtubule density on $Ca^{2+}$ signaling, Taxol treated Ocy454 cells subjected to 4 dynes/$cm^2$ fluid shear stress had reduced fluid shear stress-induced CaMKII phosphorylation and a blunted decrease in sclerostin protein, both of which were restored at 16 dynes/$cm^2$ of fluid shear stress (FIG. 3C). Immunofluorescent labeling of the microtubule network confirmed the increase in microtubule density following Taxol treatment (FIG. 3D). These results showed that increases in the density or stability of the MT network raised the threshold for fluid shear stress-induced activation of $Ca^{2+}$ influx, CaMKII signaling and sclerostin abundance.

Example 6

The Abundance of Glu-Tubulin in the MT Network Defines the Mechano-Sensitivity of Ocy454 Cells to Fluid Shear Stress Taxol induced microtubule stabilization is associated with an increase in the fraction of Glu-modified tubulin in the microtubule filament. Glu-tubulin arises from detyrosination, the enzymatic cleavage of an COOH-terminal tyrosine residue of a-tubulin by tubulin tyrosine carboxypeptidase (TTCP; protein identity unknown) leaving a glutamate (38). This reaction can be reversed by the ligation of tyrosine back to the glutamate by a tubulin tyrosine ligase (TTL). Because Glu-tubulin contributes to MT-dependent mechanotransduction in cardiac and skeletal muscle (39), its impact on osteocyte mechanotransduction was examined.

Figure 4A:
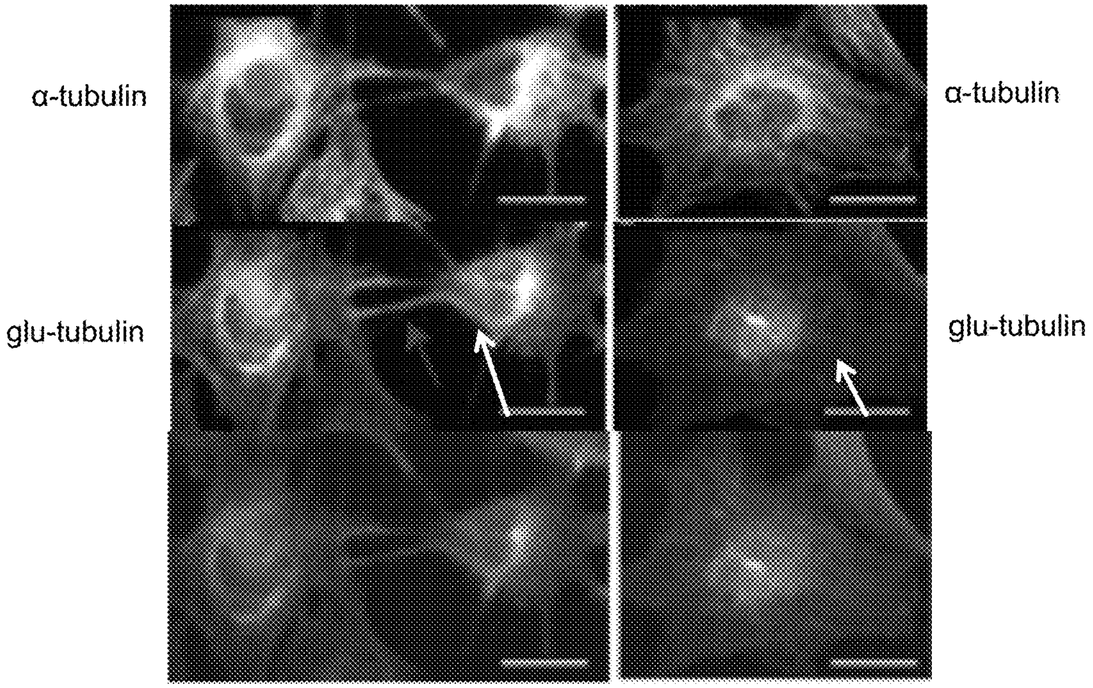
FIGS. 4A-4H show that loss of Glu-tubulin, which is found within mechanically sensitive areas of osteocytes and increased by Taxol, abrogates fluid shear stress-induced mechano-signaling.
Figure 4B:
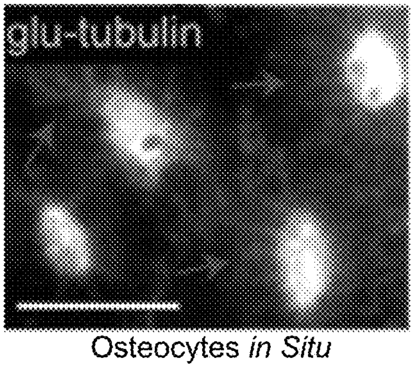
Figure 4C:
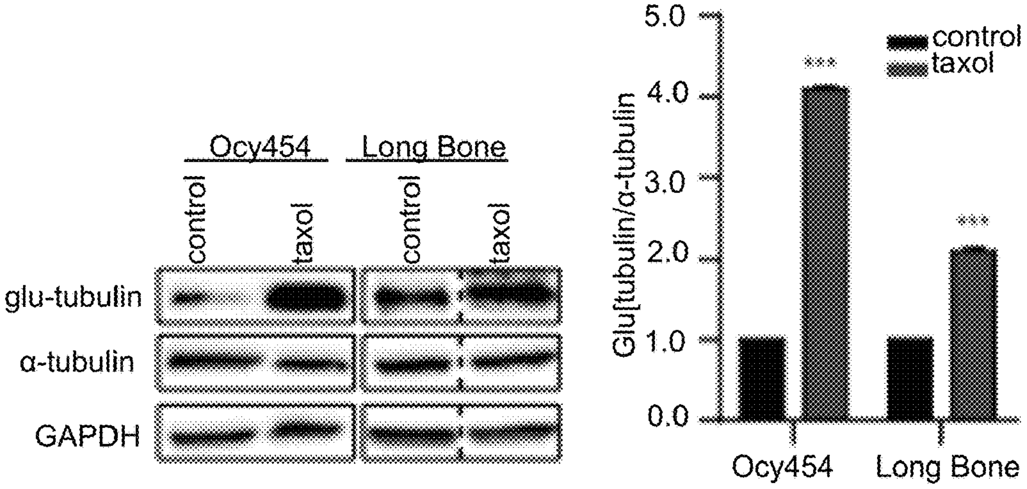
Figure 4D:
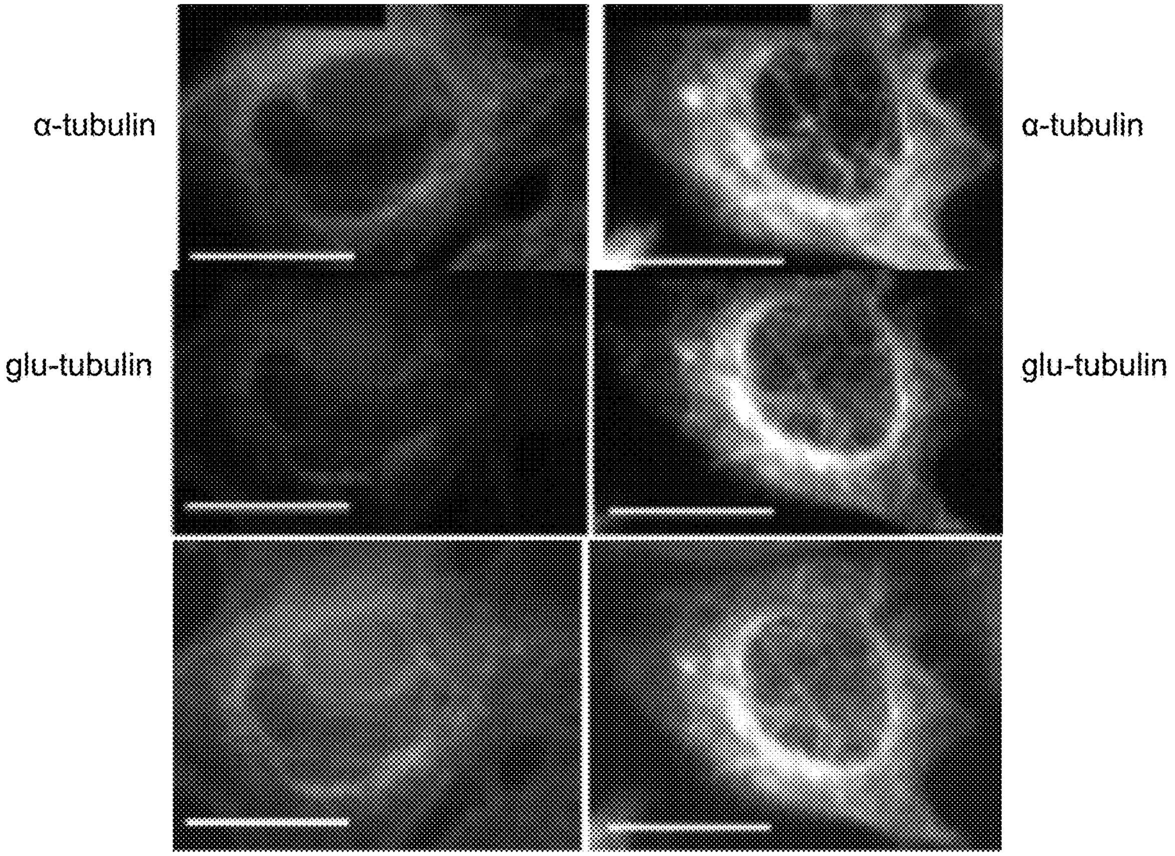

To profile the presence of Glu-tubulin in the osteocyte MT network, Ocy454 cells and murine femurs were examined by western blotting and immunofluorescence. Glu-tubulin was observed in the osteocyte cell process and primary cilia of Ocy454 cells (FIG. 4A) and in the cell processes of osteocytes in situ in formaldehyde fixed paraffin embedded sections of murine cortical bone (FIG. 4B). As observed in other tissues, Taxol treatment of Ocy454 cells in vitro or murine cortical bone ex vivo markedly increased the amount of Glu-tubulin (FIGS. 4C-4D).

Figure 4E:
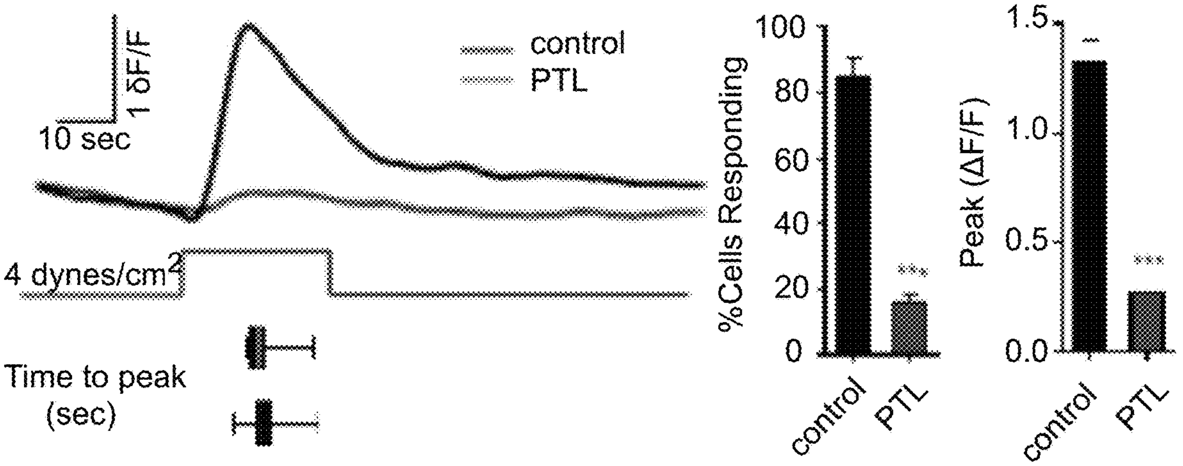
Figure 4F:
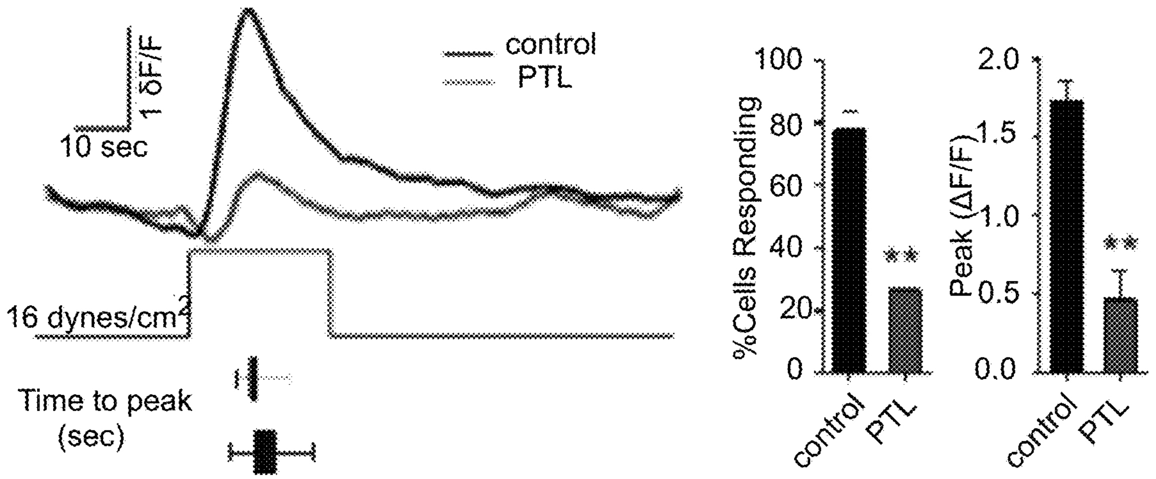
Figure 4G:
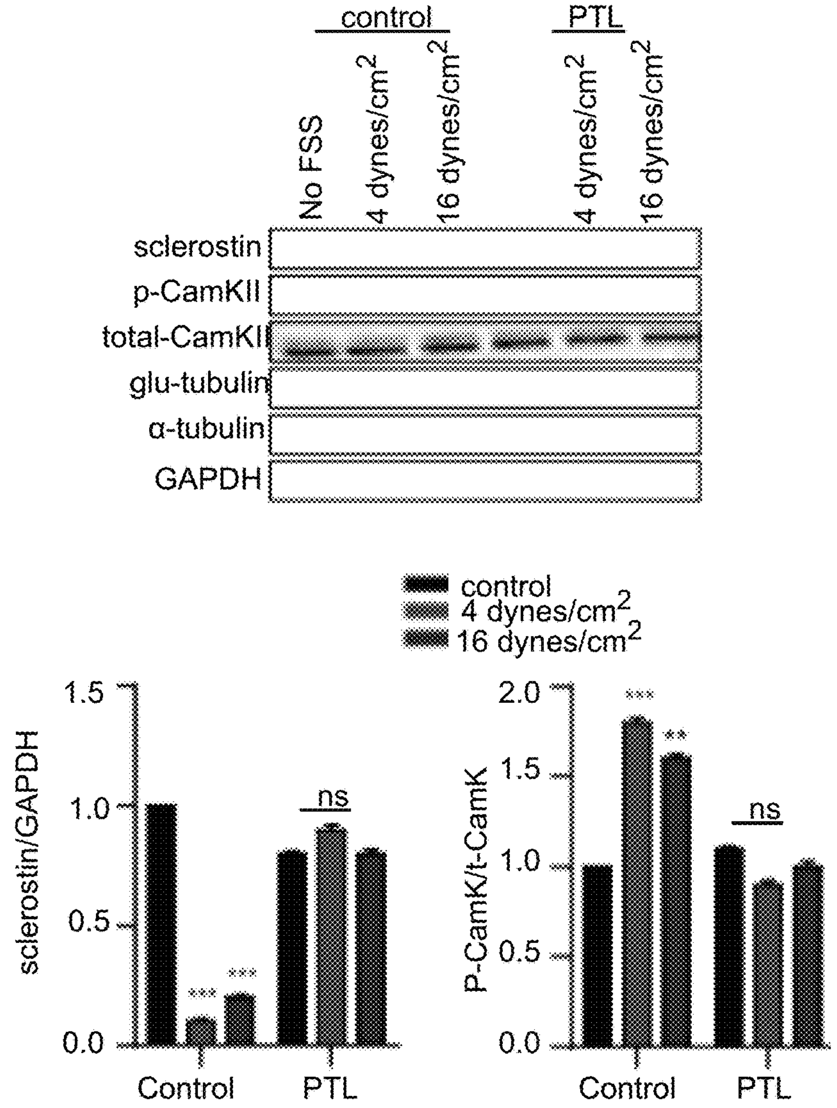
Figure 4H:
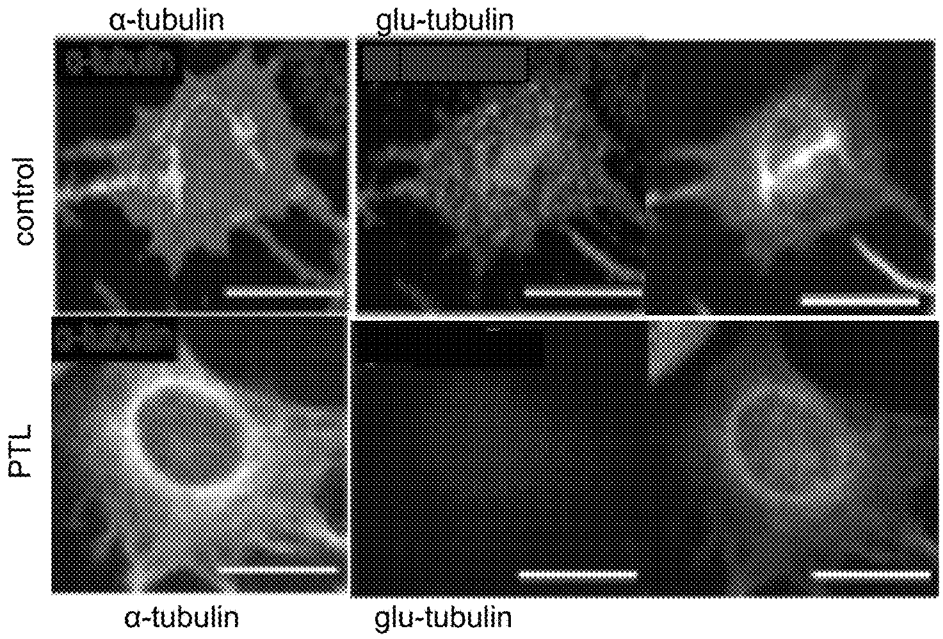

The abundance of Glu-tubulin within the microtubule network can be effectively reduced by parthenolide (PTL), a sesquiterpene lactone that inhibits the activity of the TTCP enzyme responsible for detyrosination (40). In striated muscle, the PTL-induced reduction of Glu-tubulin inhibited mechano-signaling (39), suggesting that the abundance of Glu-tubulin was the dominant regulator of mechano-activation. Real time $Ca^{2+}$ imaging of Ocy454 cells treated with PTL and exposed to FSS showed a statistically significant reduction in mechano-sensitivity (as assessed by the percentage of cells responding) and mechano-responsiveness (as assessed by the magnitude of the cellular response, peak DF/F) at both 4 and 16 dynes/$cm^2$ of FSS (FIGS. 4E-4F). Additionally, PTL treatment blunted both the FSS-induced phosphorylation of CaMKII and decrease in sclerostin abundance at both 4 and 16 dynes/$cm^2$ of FSS (FIG. 4G). These effects of PTL on mechano-responsiveness occurred with a reduction in Glu-tubulin without affecting the overall structure of the MT network (FIGS. 4G-4H). These data suggested that the amount of Glu-tubulin plays a key role in modulating osteocyte mechanotransduction.

Figure 5A:
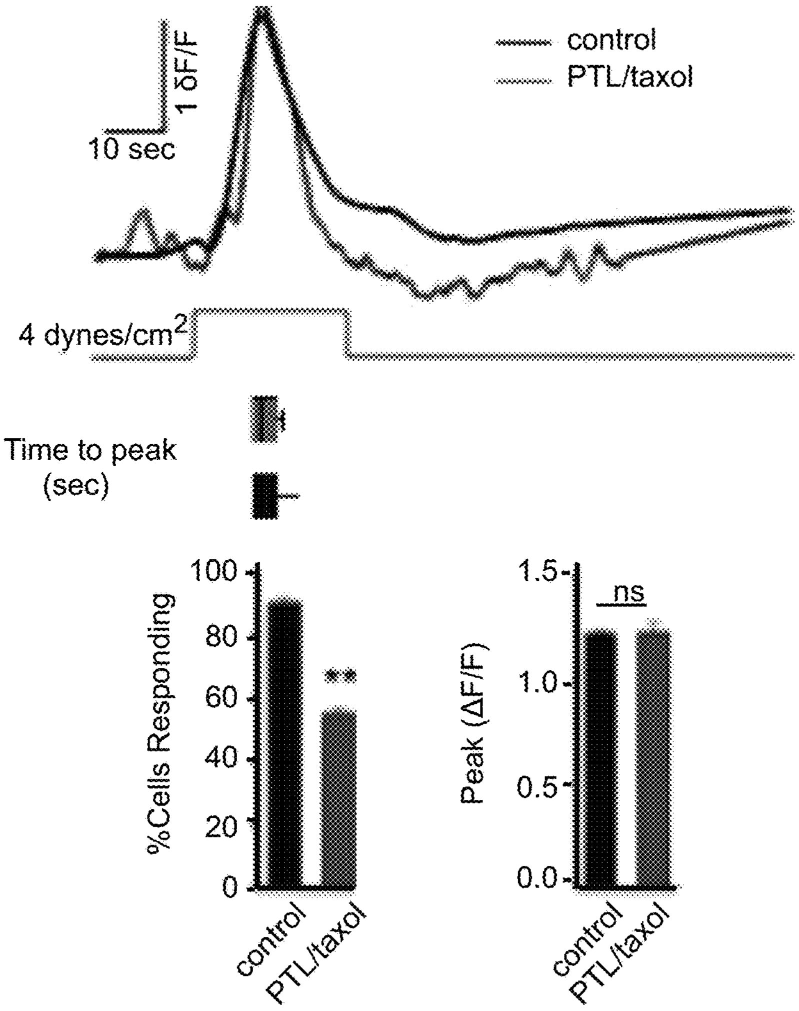
FIGS. 5A-5E show that combination treatment with parthenolide and Taxol restores mechano-signaling and alters microtubule-dependent cytoskeletal stiffness.
Figure 5B:
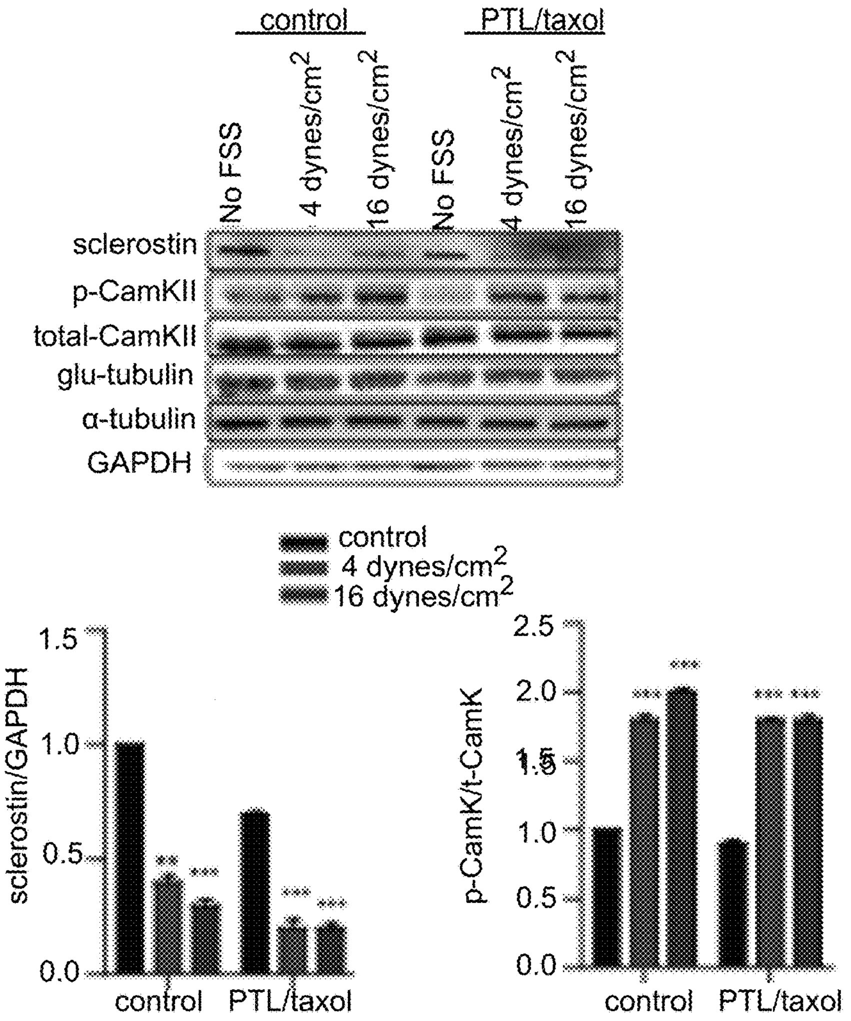
Figure 5C:
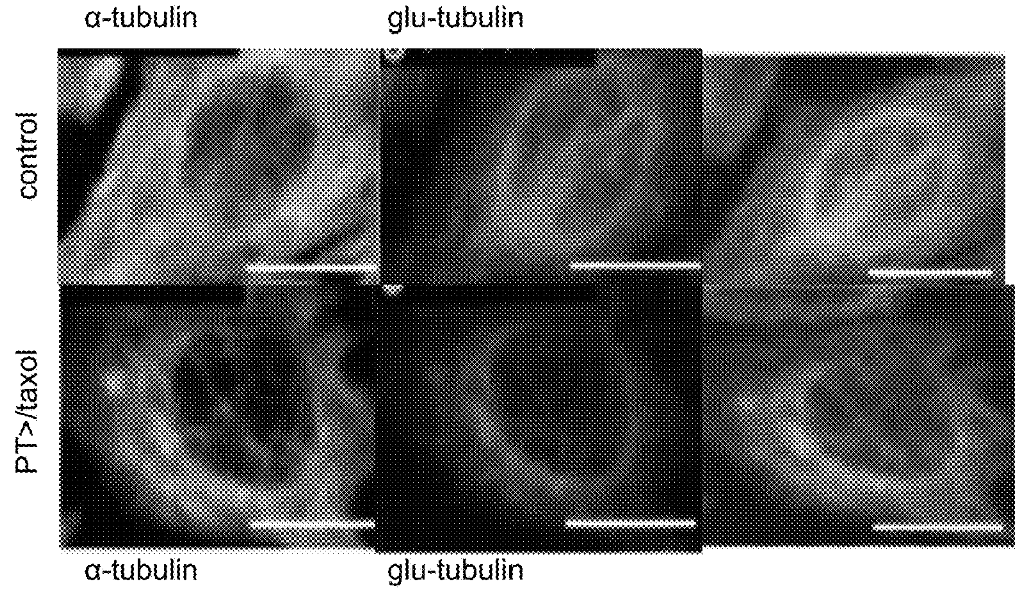

Given that Taxol increases both the density of the MT network and the amount of Glu-tubulin, the respective contributions of these alterations was determined. To this end, cells with PTL and Taxol were simultaneously treated to promote an increase in MT density while eliminating the concomitant increase in Glu-tubulin. Compared to cells treated with Taxol or PTL individually (FIGS. 3A-3D, 4A-4H), combination treatment restored mechano-responsiveness, as the FSS-induced $Ca^{2+}$ response, CaMKII phosphorylation, and decrease in sclerostin abundance at 4 dynes/$cm^2$ were rescued (FIGS. 5A-5B). Immunofluorescence microscopy of treated Ocy454 cells confirmed that the combination of Taxol and PTL resulted in the expected Taxol-driven increase in microtubule density, with PTL preventing the concomitant enhancement of Glu-tubulin (FIGS. 5B-5C). In total, these data supported that Glu-tubulin, rather than microtubule density, was the dominant regulator of the osteocyte response to fluid shear stress.

The Abundance of Glu-Tubulin Determines Cytoskeletal Stiffness in Ocy454 Cells

Figure 5D:
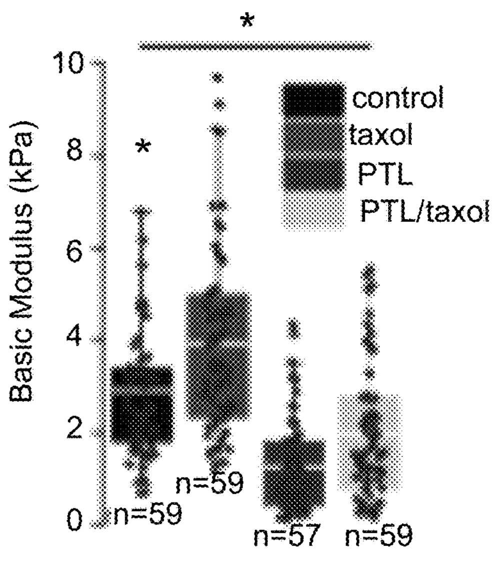
Figure 5E:
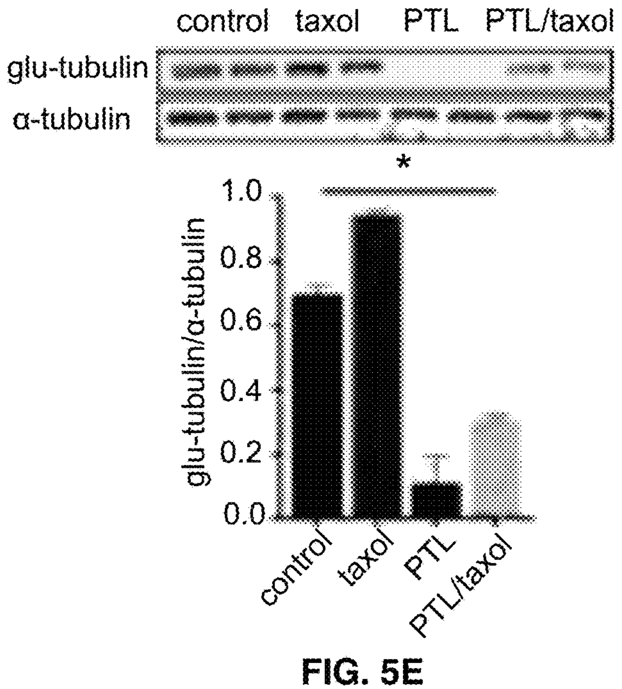

Glu-tubulin promotes microtubule interactions with other cytoskeletal elements (such as actin, intermediate filaments, and MAPs), which increases the stiffness of the cytoskeleton (24-26, 39). Accordingly, cytoskeletal stiffness was examined in Ocy454 cells. Nanoindentation atomic force microscopy (AFM) revealed that Taxol treatment increased the elastic modulus, reflecting increased cytoskeletal stiffness (FIG. 5D). Western blotting confirmed a marked increase in the Glu-tubulin in the Taxol treated cells (FIG. 5E). In contrast, PTL treated cells showed a decrease in cytoskeletal stiffness and nearly undetectable Glu-tubulin (FIGS. 5D-5E). The combination treatment with PTL and Taxol, which increased MT density while maintaining a modest amount of Glu-tubulin (FIGS. 5C-5E), resulted in an intermediate amount of cell stiffness, with an increase in the elastic modulus (increased cytoskeletal stiffness) over PTL treatment alone, yet less than that caused by Taxol treatment (FIG. 5D). When examined in the context of FSS-stimulated $Ca^{2+}$ influx, CaMKII phosphorylation, and decreased sclerostin abundance, these AFM data support a model in which cytoskeletal stiffness, which was affected by Glu-tubulin abundance, defined a permissive range for both the sensitivity and responsiveness of osteocytes to fluid shear stress.

Example 7

Figure 6A:
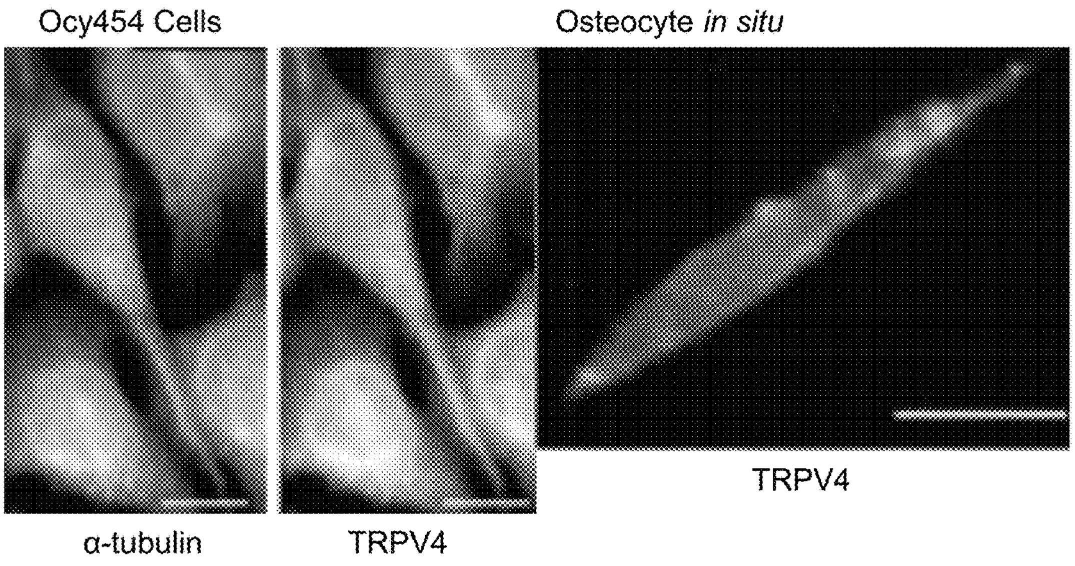
FIGS. 6A-6G show that TRPV4 is a necessary and sufficient for the osteocyte FSS-induced $Ca^{2+}$ response, CaMKII phosphorylation, and decrease in sclerostin.
Figure 6B:
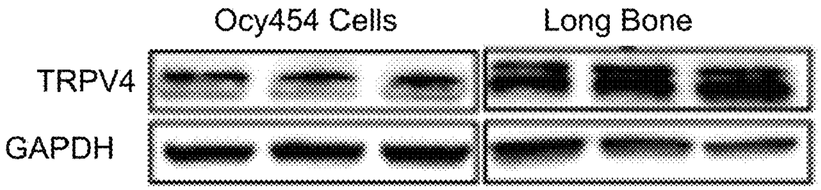

Ocy454 FSS-Induced Calcium Influx is Mediated by TRPV4 qRT-PCR was used to establish the expression profile of mRNAs encoding $Ca^{2+}$ channel(s) implicated in osteocyte $Ca^{2+}$ signaling. Trpv4 was particularly abundant at the mRNA level and was an attractive candidate given evidence that Trpv4 has been implicated in microtubule-dependent mechanotransduction in other cell types (44-46). Consistent with the abundance of Trpv4 transcript, immunofluorescence staining of Ocy454 cells and paraffin embedded murine cortical bone sections showed the presence of TRPV4 in osteocytes (FIG. 6A). Western blot analysis of Ocy454 cells and murine long bone extracts confirmed the presence of TRPV4 protein (FIG. 6B).

Figure 6C:
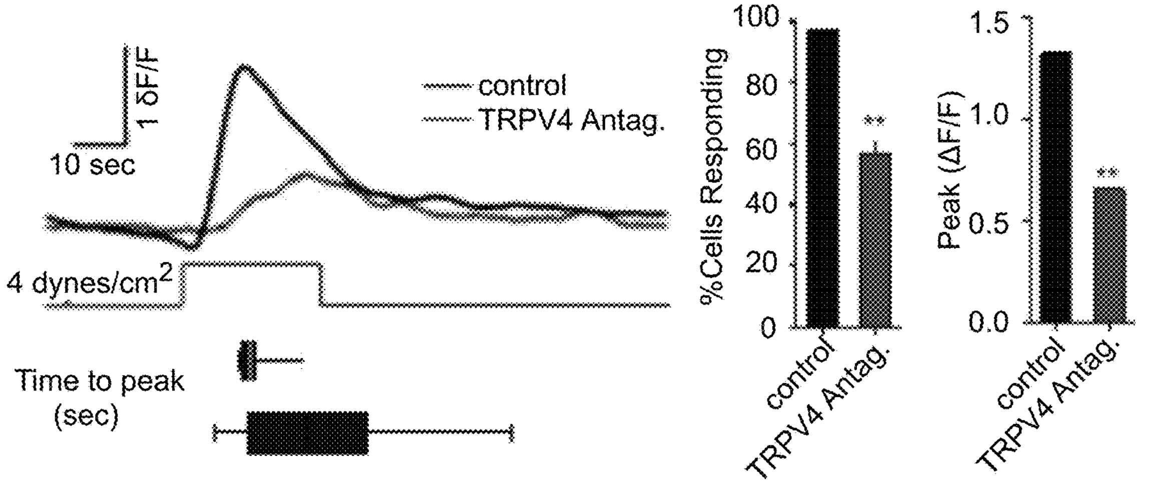
Figure 6D:
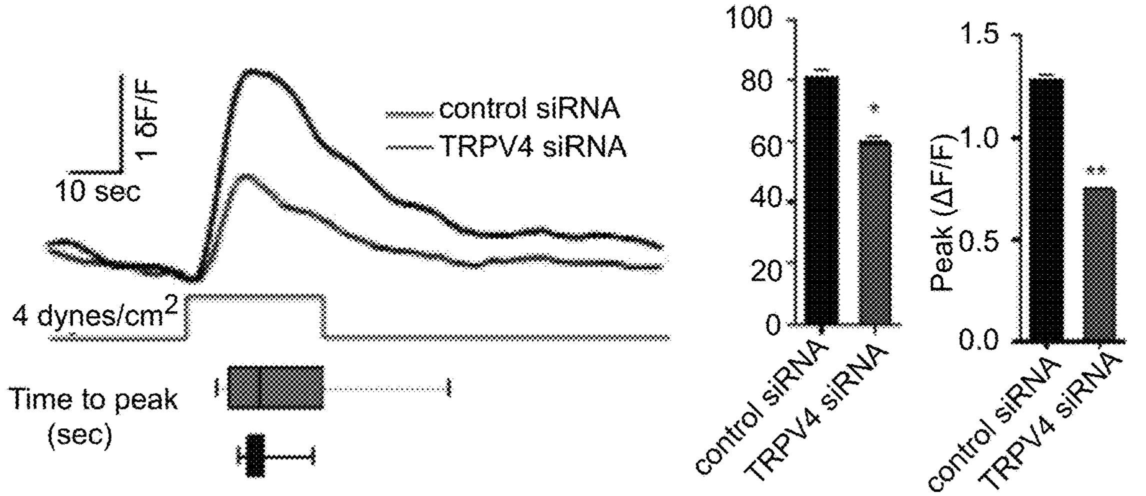

To determine the impact of TRPV4 on FSS-triggered mechanotransduction, Ocy454 cells were treated with GSK2193874, a TRPV4 antagonist. The data revealed a statistically significant decrease in mechano-sensitivity (as assessed by the percentage of cells responding) and mechano-responsiveness (as assessed by peak $Ca^{2+}$ response) in GSK2193874 treated Ocy454 cells (FIG. 6C). Additionally, transfection of Ocy454 cells with TRPV4 targeting siRNA (FIG. 6D) yielded similar results to the pharmacological antagonist, supporting the conclusion that TRPV4 was a major contributor to $Ca^{2+}$ influx pathway acutely activated by fluid shear stress.

Figure 6E:
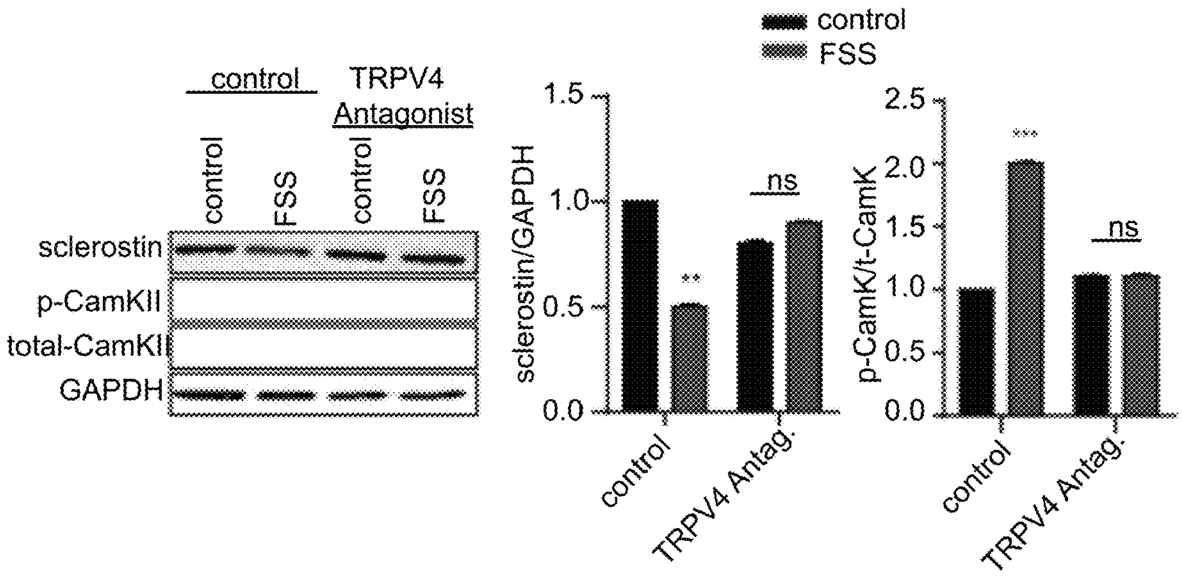
Figure 6F:
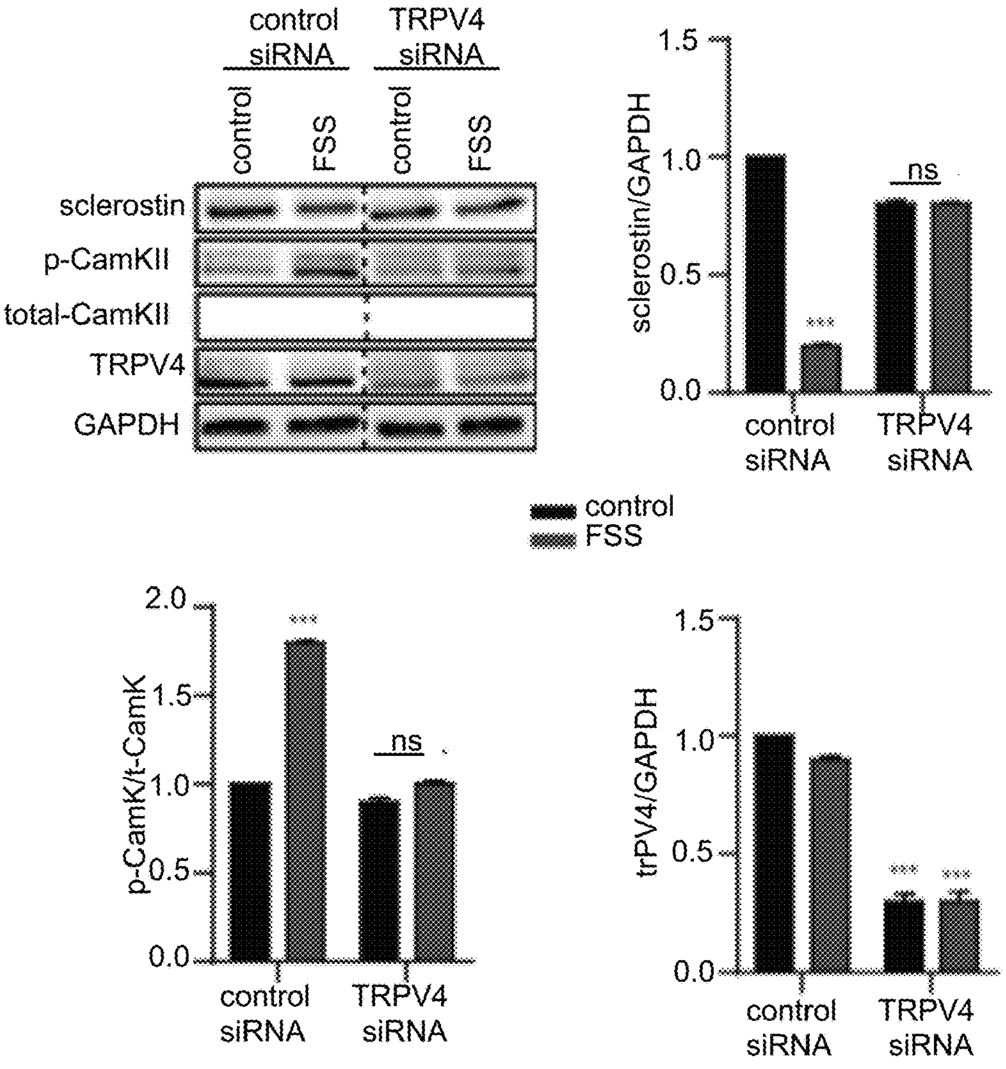
Figure 6G:
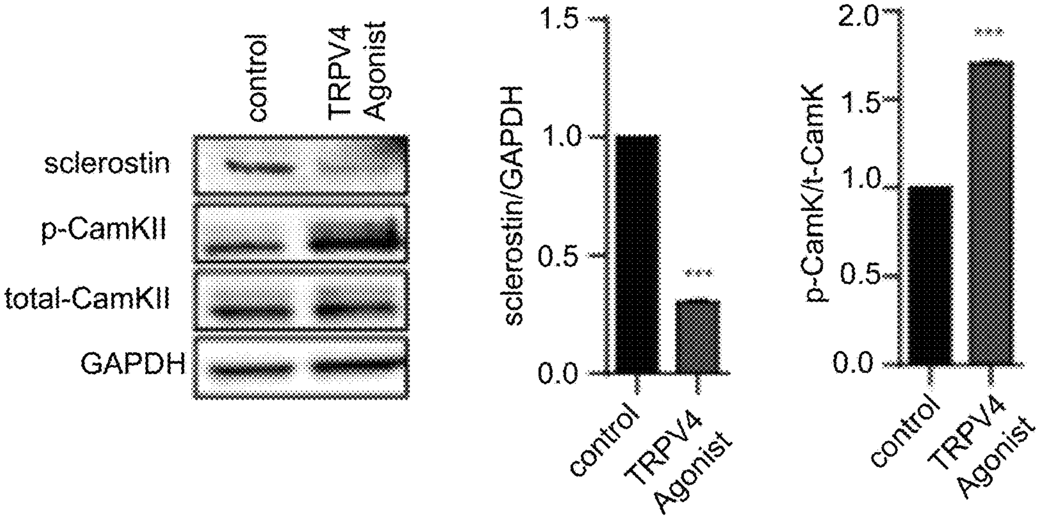

Consistent with TRPV4 as the source of fluid shear stress induced $Ca^{2+}$ influx, Ocy454 cells treated with the TRPV4 antagonist or transfected with siRNA specific to TRPV4 showed a reduction in fluid shear stress-induced CaMKII phosphorylation and a blunted FSS-induced downregulation of sclerostin (FIGS. 6E-6F). Conversely, treating Ocy454 cells with the TRPV4 agonist GSK-1016790A recapitulated the mechano-response, including the reciprocal activation of CaMKII and reduction in sclerostin protein independently of fluid shear stress (FIG. 6G), demonstrating that TRPV4 activation was sufficient to phosphorylate CaMKII and decrease sclerostin.

Example 8

TRPV4 Opens in Response to FSS-Induced ROS

Figure 7A:
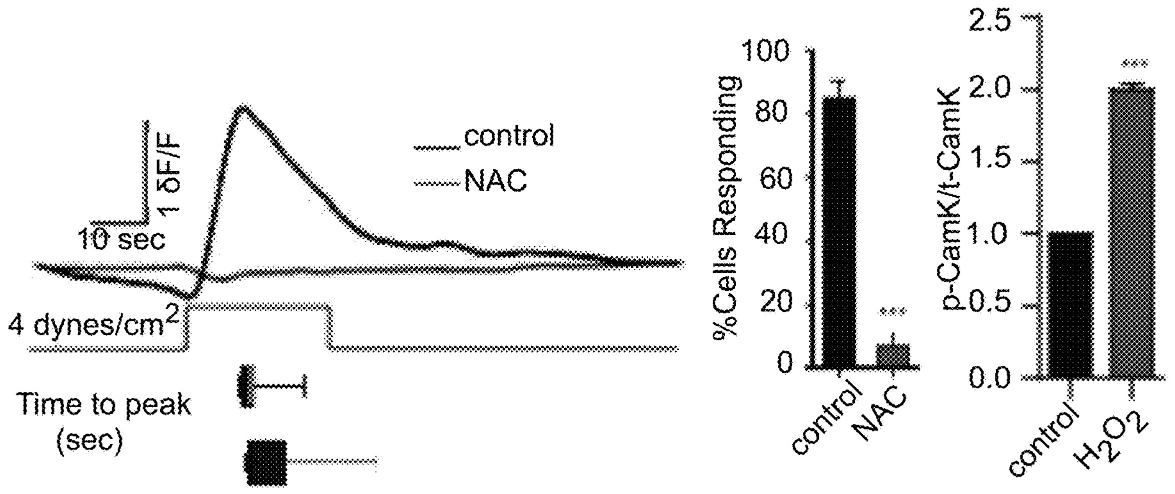
FIGS. 7A-7D show that ROS is required for the fluid shear stress-induced $Ca^{2+}$ response, CaMKII phosphorylation, and decrease in sclerostin.
Figure 7B:
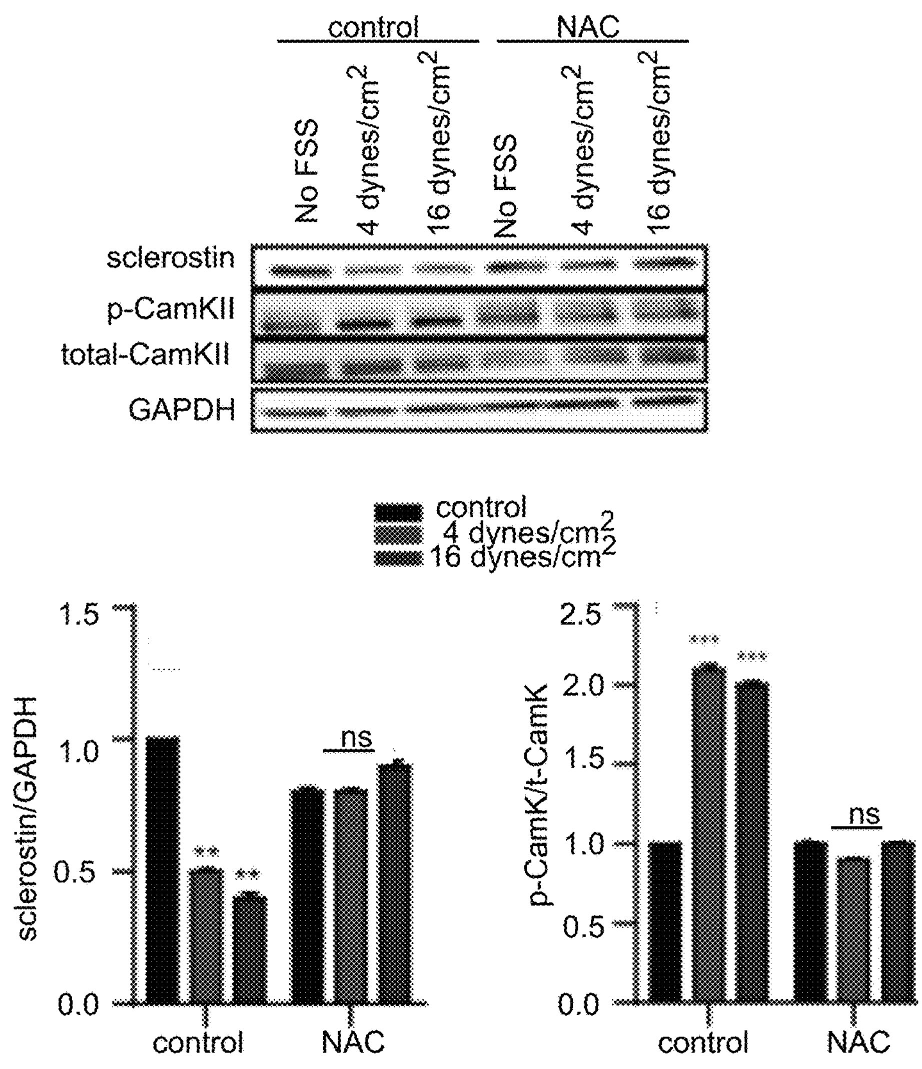
Figure 7C:
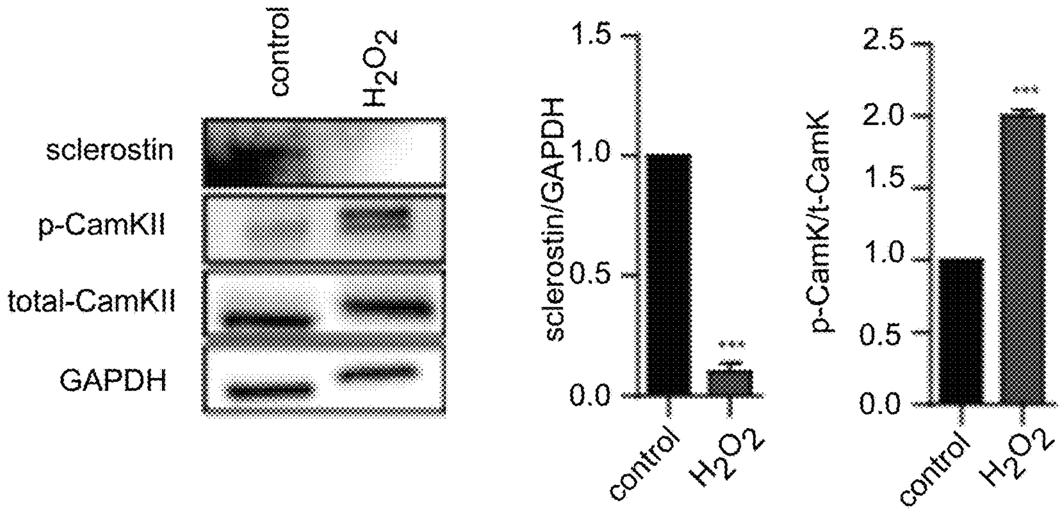

TRPV4 can be activated by mechanical stimuli through direct tethering to the cytoskeleton (44) or by ROS-dependent oxidation (47-48). To assess the impact of ROS-mediated activation, Ocy454 cells were treated with the ROS scavenger N-acetylcysteine (NAC). Real-time, live cell $Ca^{2+}$ imaging showed that NAC treatment abrogated the fluid shear stress-induced response at both 4 and 16 dynes/$cm^2$ (FIG. 7A). Likewise, a reduction in CaMKII phosphorylation and a blunting of the FSS-induced decrease in sclerostin protein was observed in NAC treated cells (FIG. 7B). Hydrogen peroxide ($H_2O_2$) challenge to Ocy454 cells reciprocally increased phospho-CaMKII and reduced sclerostin protein independently of FSS (FIG. 7C), thus supporting ROS as the signal downstream of mechano-activation. To confirm this observation, Ocy454 cells were simultaneously imaged for ROS using CellROX and $Ca^{2+}$ using Fluo-4.

Figure 7D:
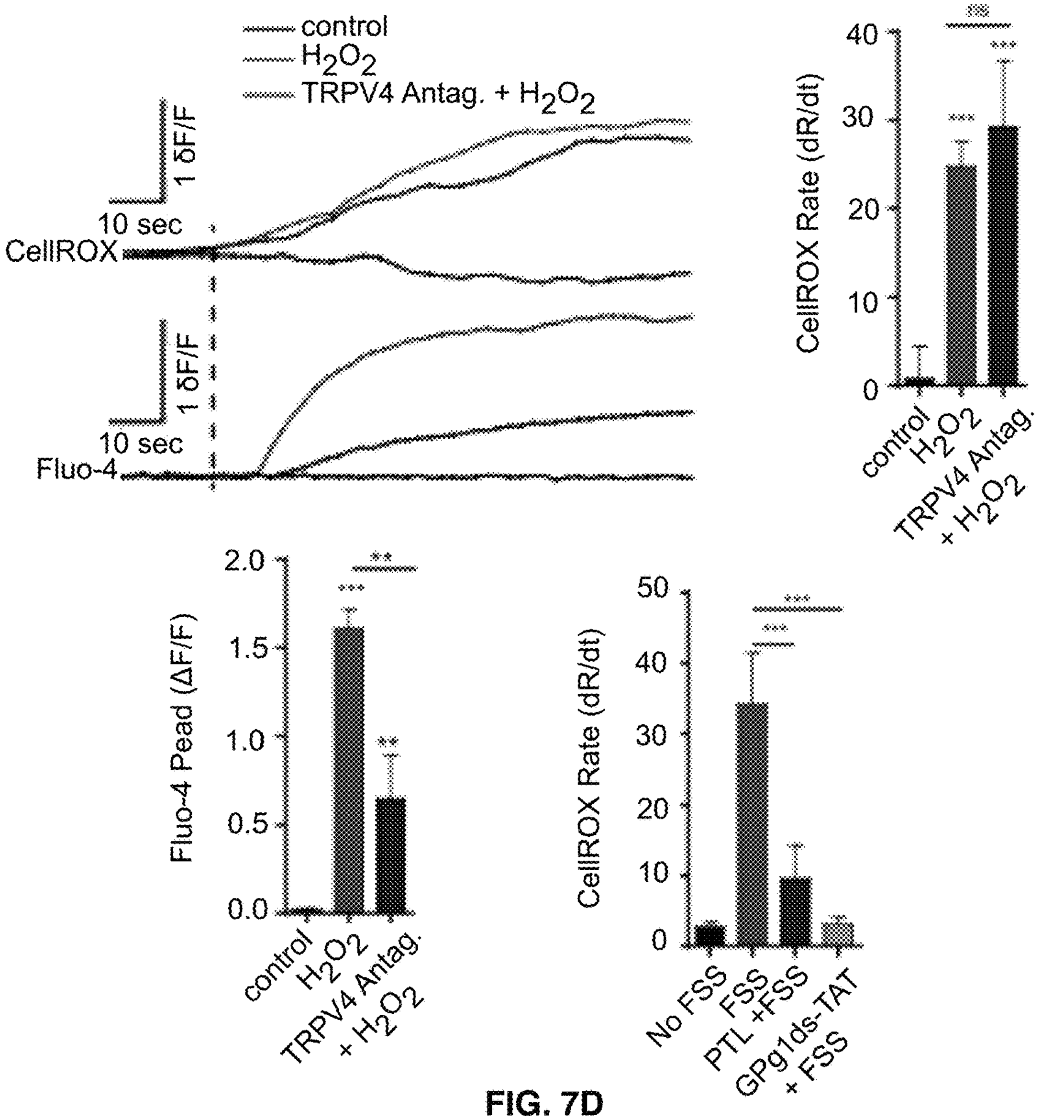

Treatment with $H_2O_2$ stimulated both ROS and intracellular $Ca^{2+}$ (FIG. 7D). Treatment with a TRPV4 antagonist blunted the $H_2O_2$-induced $Ca^{2+}$ influx without affecting ROS (FIG. 7D). Activation of TRPV4 in Ocy454 cells with the TRPV4 agonist was insufficient to induce ROS production. In aggregate, these data established ROS as a necessary, upstream regulator of TRPV4-dependent $Ca^{2+}$ influx.

Example 9

FSS-Induced ROS Signaling is Mediated by the Mechano-Sensitive ROS Generating Enzyme NOX2

Figure 8A:
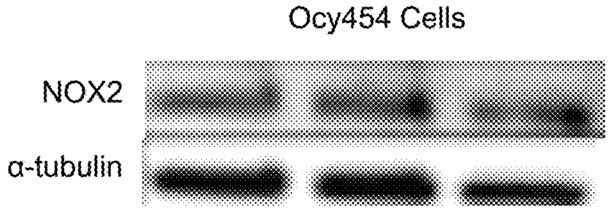
FIGS. 8A-8E show that NOX2 generates ROS in response to fluid shear stress and is required for fluid shear stress-induced $Ca^{2+}$ response, CaMKII phosphorylation and decrease in sclerostin.
Figure 8B:
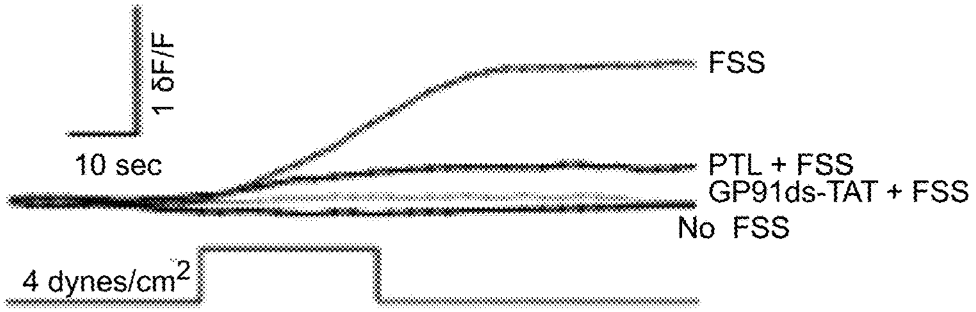
Figure 8C:
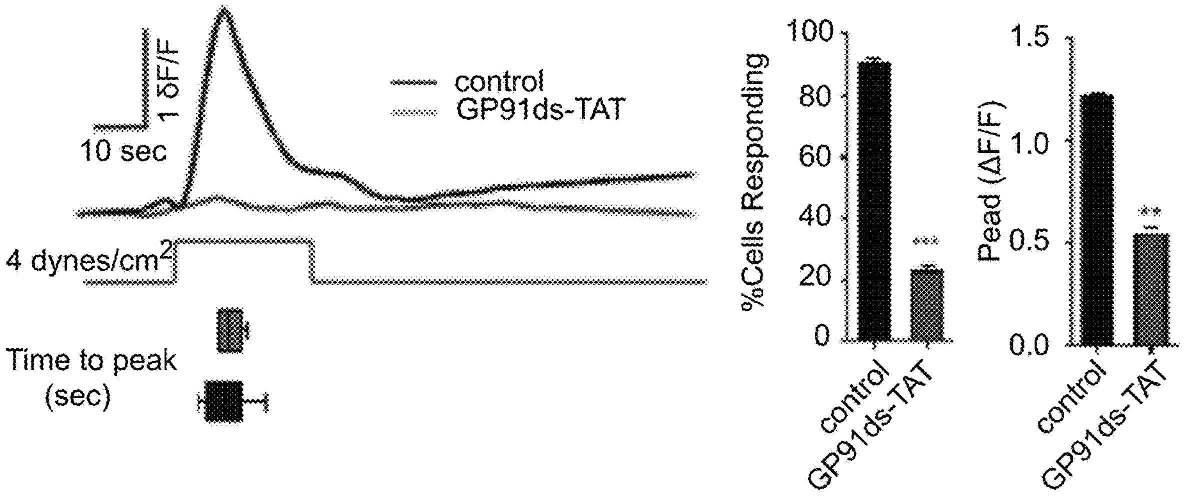
Figure 8D:
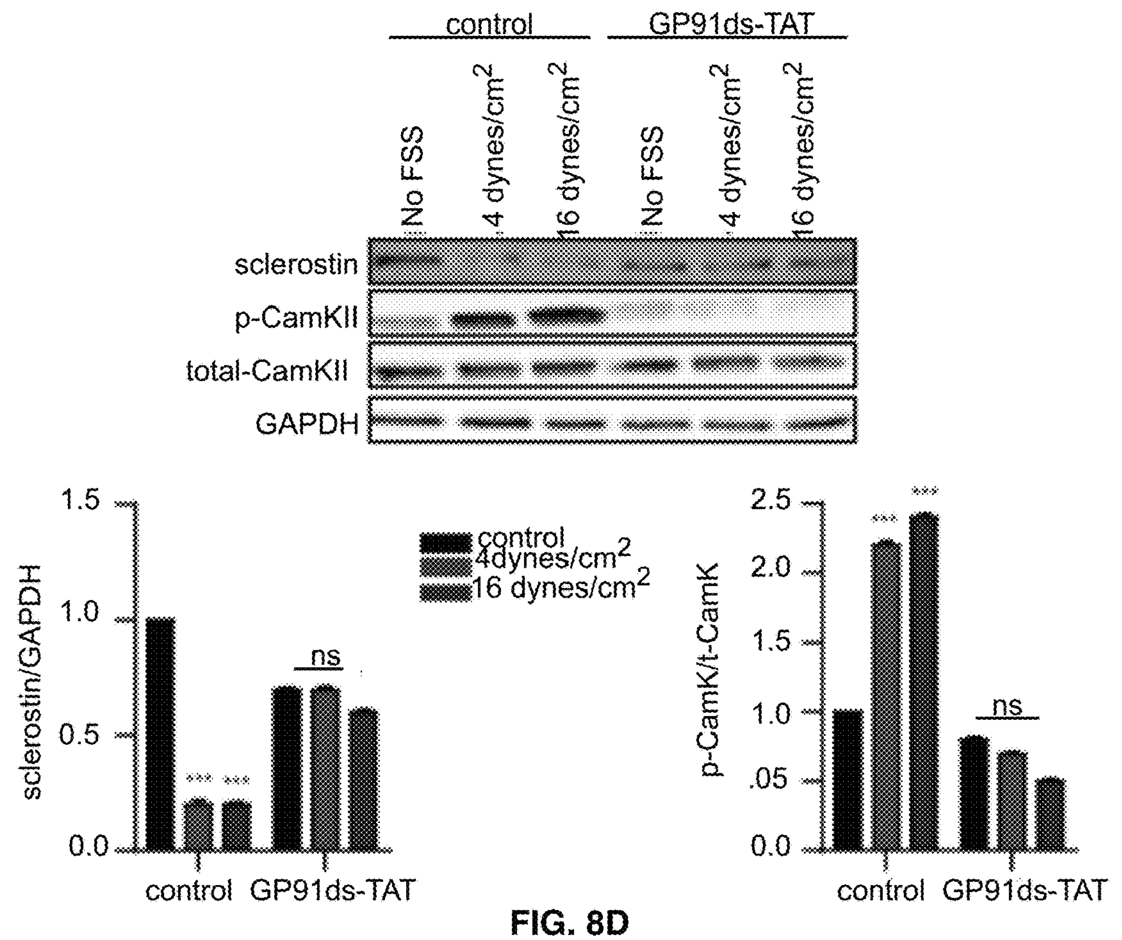

NOX2 is a mechano-sensitive ROS generating enzyme implicated in MT-dependent ROS signaling (39, 49-51). Western blot confirmed the presence of NOX2 in Ocy454 cells (FIG. 8A). Exposure of Ocy454 cells to 4 dynes/$cm^2$ FSS elicited the production of ROS, as measured by CellROX, an effect that was blunted by treatment with PTL, to inhibit Glu-tubulin, or the NOX2 inhibitor GP91ds-TAT (FIG. 8B). Likewise, when GP91ds-TAT treated Ocy454 cells were subjected to FSS and monitored for intracellular $Ca^{2+}$, both mechano-sensitivity (as assessed by the percentage of cells responding) and mechano-responsiveness (as assessed by peak $Ca^{2+}$ response) were attenuated (FIG. 8C). Unlike stiffening the MT network with Taxol, which could be overcome with increased FSS, the NOX2 inhibition persisted at higher flow rates, confirming NOX2 as a convergence point in this mechanotransduction cascade. In addition, inhibition of NOX2 with GP91ds-TAT blocked the phosphorylation of CaMKII by fluid shear stress and reduced the fluid shear stress-induced decrease in sclerostin at both 4 and 16 dynes/$cm^2$ (FIG. 8D). These data implicated NOX2 as the source of ROS that activates TRPV4-dependent $Ca^{2+}$ influx during fluid shear stress.

Example 10

Effect of Targeting Microtubules with Cochicine on Aged Mice

Colchicine Reduces Sclerostin and Enhances Bone Formation

Figure 9:
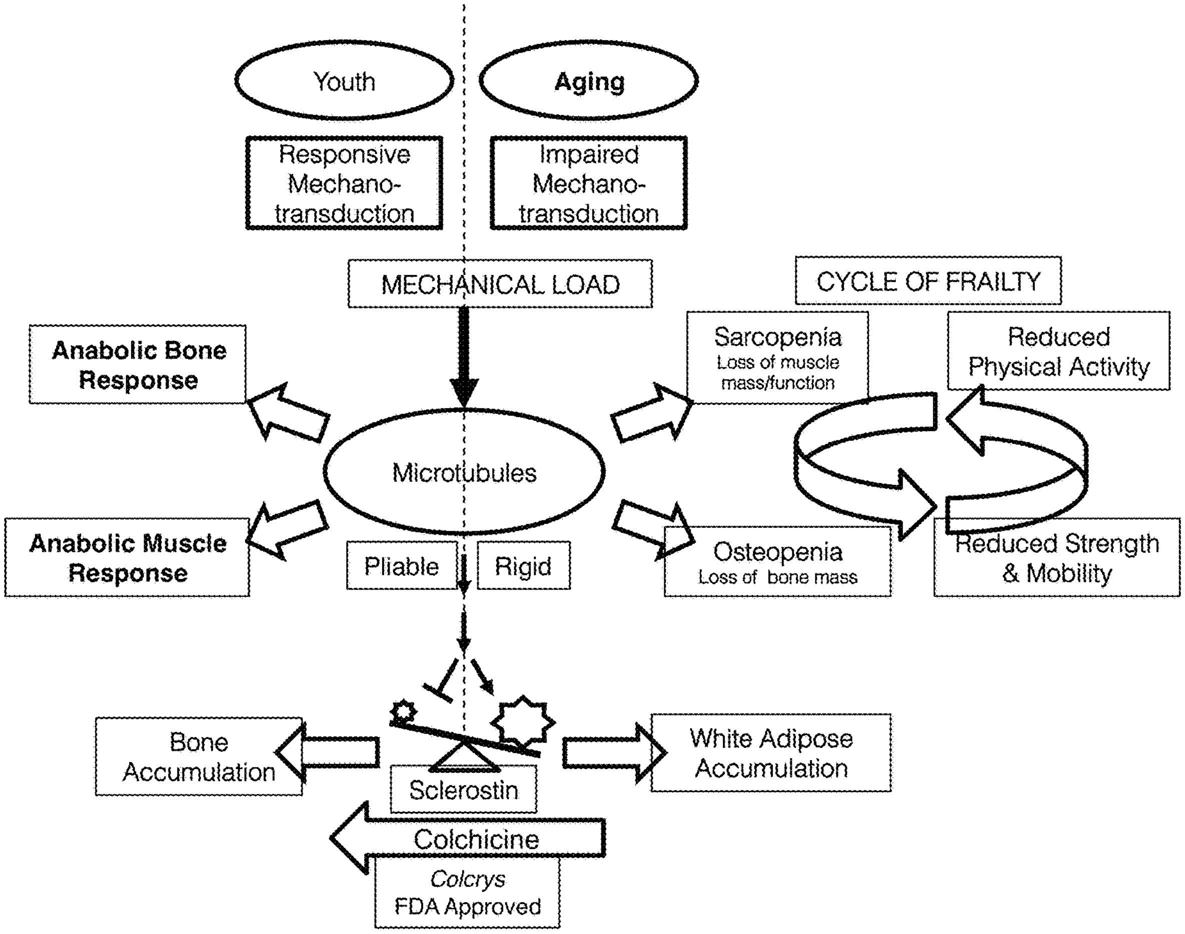
FIG. 9 illustrates the mechanism of action of microtubules in young and aging subjects.

FIG. 9 illustrates the mechanism of responsive and impaired mechanotransduction on microtubules in young mice and aged mice. As age increases a cycle of frailty occurs due to a loss of muscle mass and function and a loss of bone mass resulting in reduced strength and mobility followed by reduced physical activity and an accumulation. Reduced physical activity further increases loss of muscle and bone masses. It is demonstrated that colchicine increases bone accumulation and reduces accumulation of white adipose in aged mice.

Figure 10A:
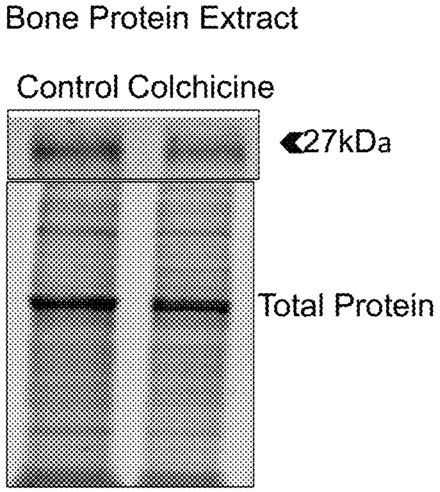
FIGS. 10A-10D compares the effects of colchicine on young mice (16 weeks) and aged mice (78 weeks) on sclerostin levels (FIG. 10A), on bone mineral density (FIGS. 10B-10D).
Figure 10B:
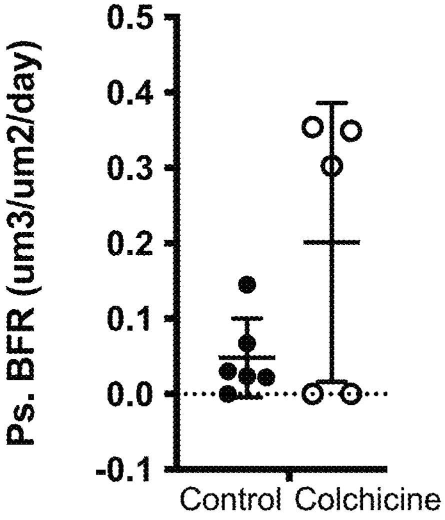
Figure 10C:
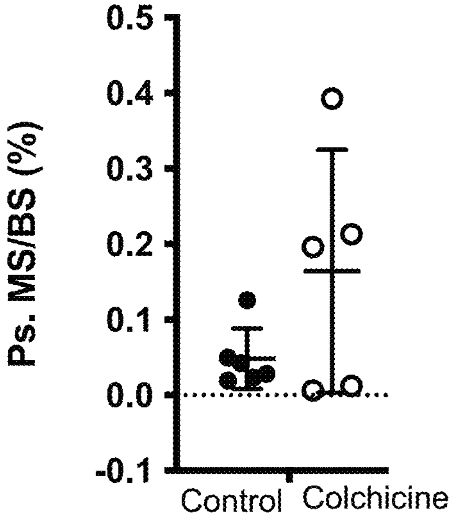
Figure 10D:
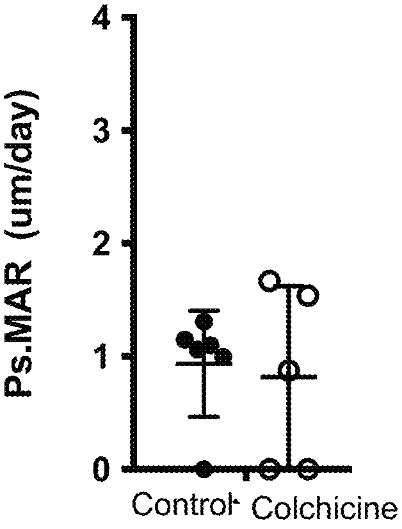

Young, 16 weeks, mice and old, 78 weeks, mice were treated for 8 weeks with 1 mg/L of colcrys (FDA approved colchicine) in drinking water followed by euthanasia for studying bone formation (n=6 control mice where 2 controls died during the study and n=8 colchicine mice where 3 colchicine mice had no evidence of bone label due to injection of the fluor into the urinary bladder). Treating the aged mice with colchicine, which targets microtubule density, decreased bone derived sclerostin, an inhibitor of bone formation, (FIG. 10A) and increased bone formation rate (BFR) (FIG. 10B-10D) on the cortical bone perimeter, likely through bone formation along the surface of bone (mineralizing surface/bone surface, MS/BS) rather than altering the action of individual osteoblasts (mineral apposition rate, MAR).

Figure 11A:
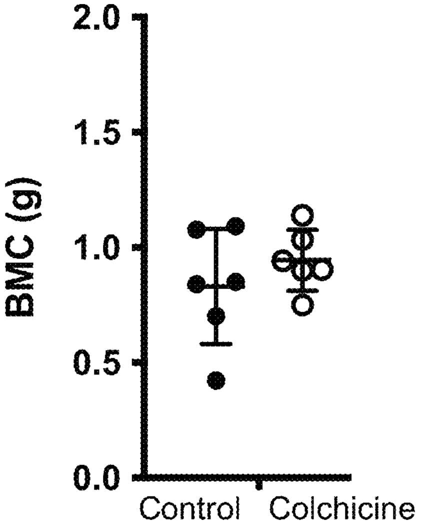
FIGS. 11A-11D compares the effects of colchicine on the young mice and the aged mice on bone mineral content (BMC) (FIG. 11A) and bone mineral density (BMD) (FIG. 11B), cortical bone volume (Ct.TV) (FIG. 11C) and polar mean moment of inertia (MMIp) (FIG. 11D).
Figure 11B:
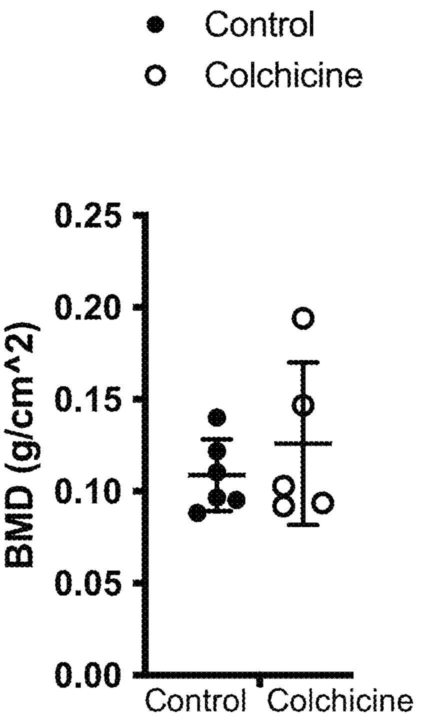
Figure 11C:
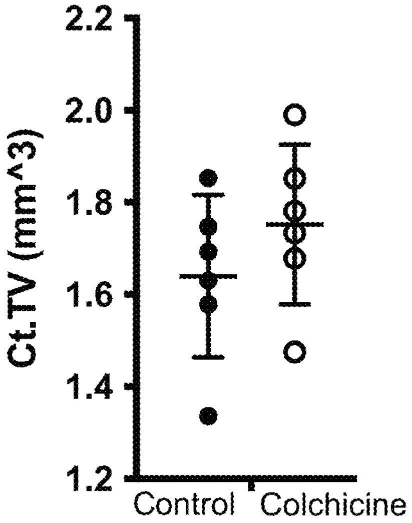
Figure 11D:
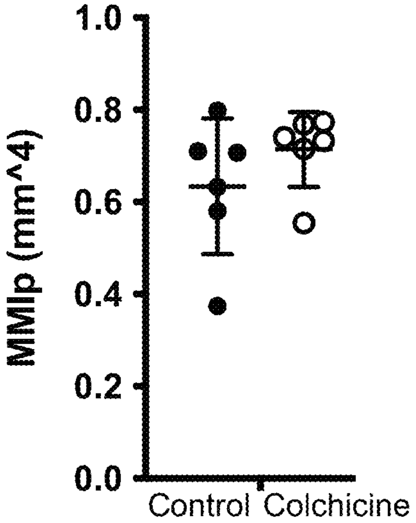

Colchicine treatment tended towards increases in bone mineral content (BMC) (FIG. 11A) and bone mineral density (BMD) (FIG. 11B) by whole body dual-energy x-ray absorptiometry (DEXA) and cortical bone volume (FIG. 11C) and polar mean moment of inertia (FIG. 11D), which is a geometric prediction of bone strength, by micro computed tomography (microCT). No changes were observed in trabecular bone mass over the 8 weeks, but it is contemplated that a longer treatment period would yield significant results.

Colchicine Improves Muscle Power and Reduces Adipose Tissue

Figure 12A:
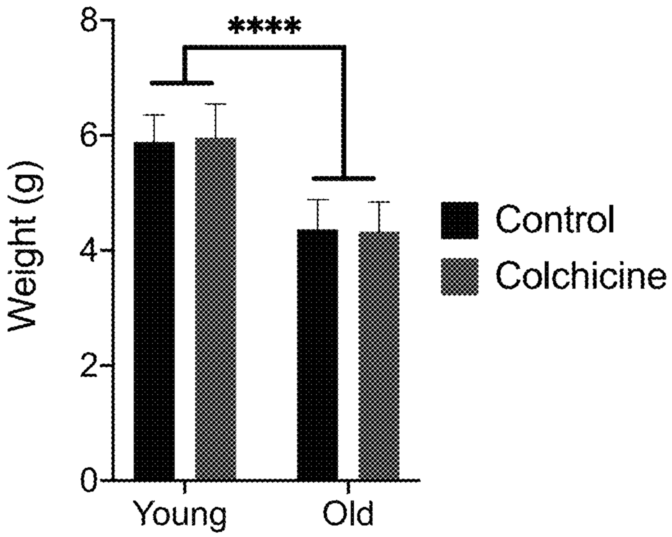
FIGS. 12A-12C compares the effects of colchicine on young mice and the aged mice on muscle mass (FIG. 12A), maximum contraction velocity (FIG. 12B) and maximum muscle power (FIG. 12C).
Figure 12B:
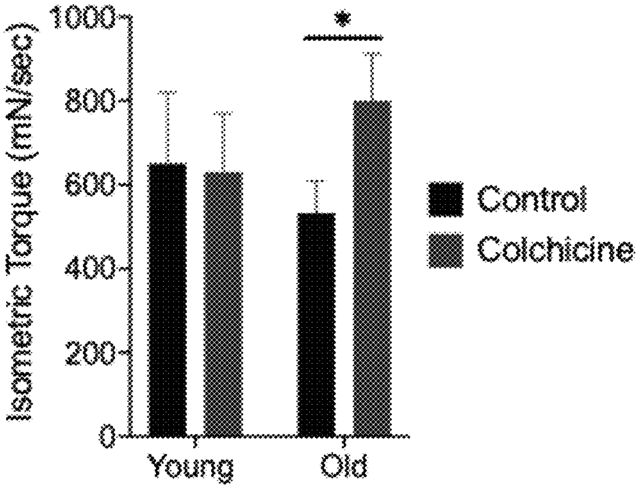
Figure 12C:
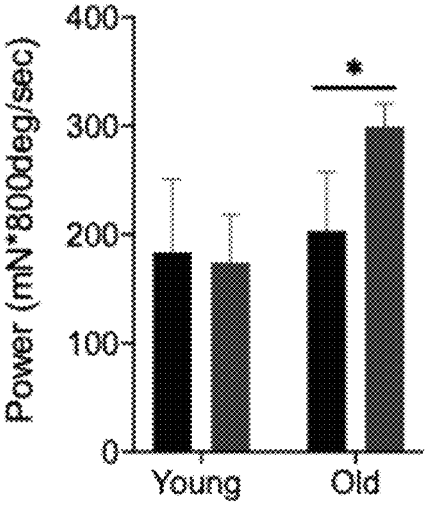

Young and aged mice were treated with colchicine as per the bone formation study followed by euthanasia and muscle testing. After 8 weeks aged mice had increased muscle power. Although colchicine did not increase muscle mass in the gastrocnemius muscle (FIG. 12A), an increase in maximum contraction velocity (FIG. 12B) and maximum muscle power (FIG. 12C) was demonstrated.

Figure 13A:
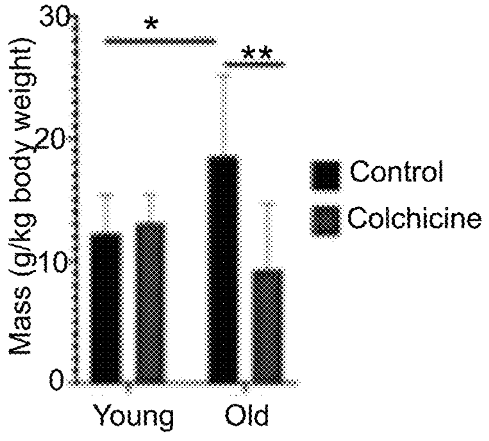
FIGS. 13A-13E compares the effects of colchicine on the young mice and the aged mice on inguinal fat (FIG. 13A), gonadal fat (FIG. 13B) and body weight (FIG. 13C) and shows the reduction in adipocyte area in aged mice (FIGS. 13D-13E).
Figure 13B:
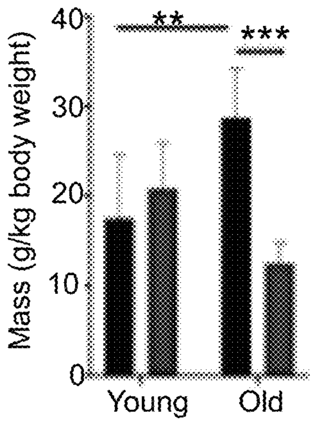
Figure 13C:
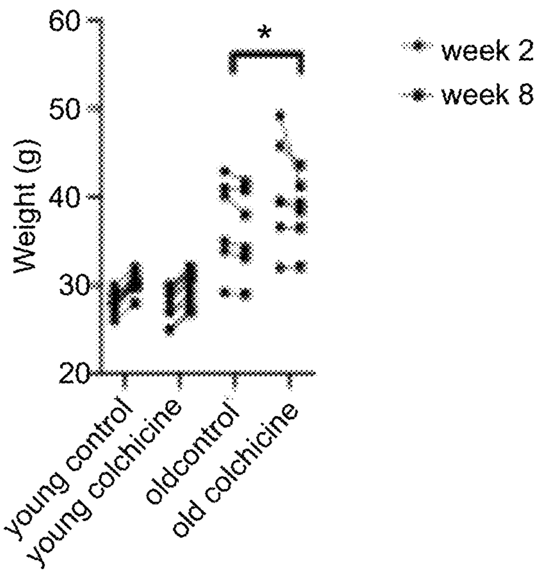
Figure 13D:
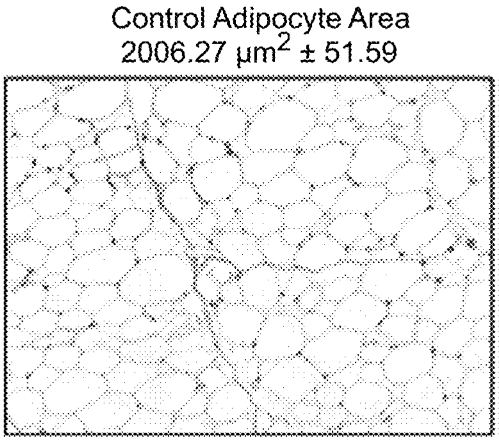
Figure 13E:
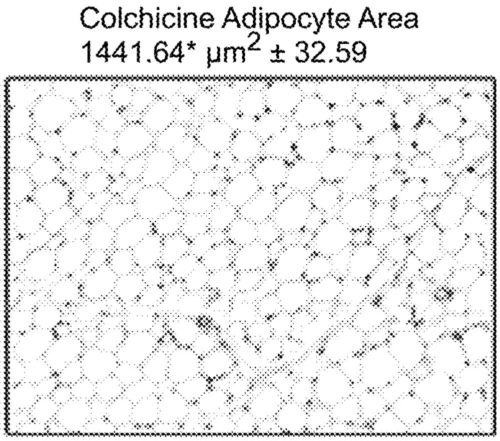

Sclerostin decreases white adipose tissue in aged mice. Bone derived sclerostin regulates not only bone formation but reduces white adipose tissue. FIGS. 13A-13C demonstrate that colchicine reduced white adipose tissue, i.e., inguinal fat and gonadal fat as evidenced by change in body weight in aged mice. Adipocyte area in control mice of 2006.27 $\mu m^2 \pm 51.59$ (FIG. 13D) was reduced to 1441.64*$\mu m^2 \pm 32.59$ (FIG. 13E).

DISCUSSION

Figure 8E:
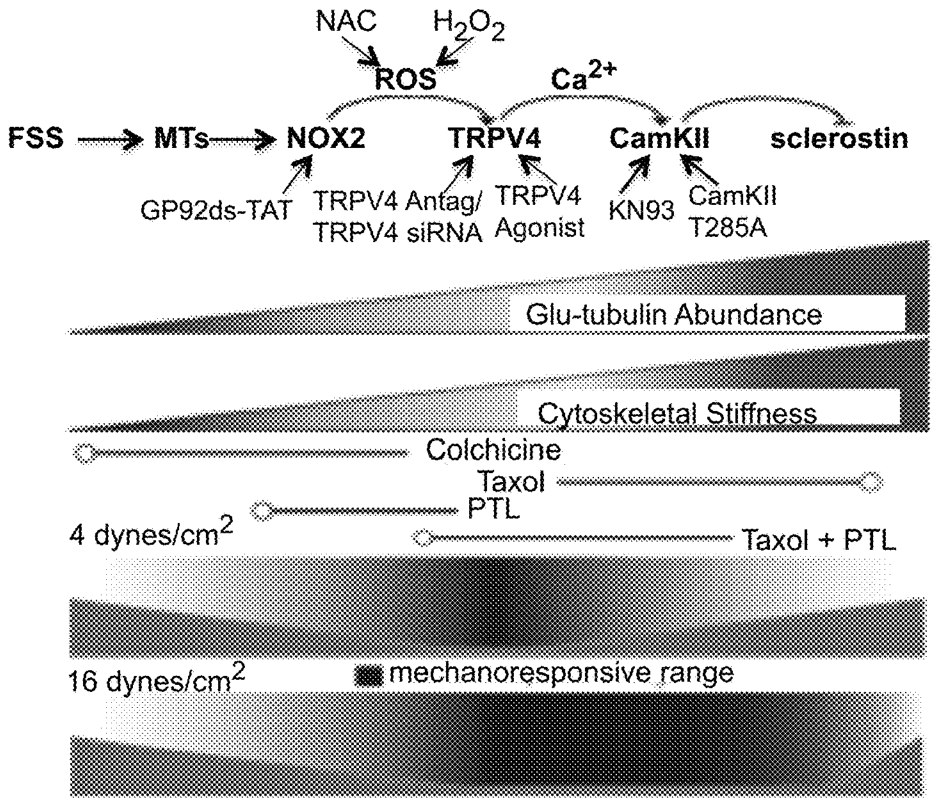

The present invention demonstrates that a mechanotransduction pathway in osteocytes that links fluid shear stress to the activation of $Ca^{2+}$ influx that drives the mechanically-induced downregulation of sclerostin. Central to this discovery was that the microtubule network, and more specifically the abundance of Glu-tubulin that defined the cytoskeletal stiffness, determined the mechano-sensitivity of osteocytes to fluid shear stress. Upon a threshold amount of fluid shear stress, MT-dependent activation of NOX2 elicited ROS that activated TRPV4-dependent $Ca^{2+}$ influx signals and CaMKII phosphorylation, driving sclerostin downregulation in osteocytes (FIG. 8E). The present data revealed new molecular players and provided insights into osteocyte mechanotransduction.

The present data showed that microtubules are, at minimum, required for mechano-signaling, consistent with reports on other mechano-signaling events in bone (31-34). The present invention demonstrates that the microtubule network, and specifically its abundance of Glu-tubulin, were critical regulators of cytoskeletal stiffness, which tuned the mechano-responsive range at which osteocytes were activated by fluid shear stress. A targeted reduction in Glu-tubulin abundance (induced through PTL treatment) decreased MT-dependent cytoskeletal stiffness, impairing the osteocytes ability to sense and transduce mechanical cues (FIG. 8E). In contrast, driving up the abundance of Glu-tubulin increased cytoskeletal stiffness, which increased the amount of fluid shear stress needed to activate the mechanotransduction pathway. Thus, the cytoskeleton becomes a dynamic integrator of mechanical cues, affecting the mechanical set point at which an osteocyte can respond to a given mechanical load. The present discovery that MTs were central to this mechanotransduction pathway may unify several models of osteocyte mechano-sensing. The primary cilia hypothesis (16, 18, 37), the integrin-based mechanosome (14, 15) and perhaps even the opening of Cx43 hemichannels response to mechanical activation of integrins (17) are all based on structures linked to the microtubule network.

Another finding was that TRPV4 was a major pathway for the initial and rapid FSS-induced $Ca^{2+}$ influx that drives sclerostin downregulation in osteocytes. Unlike modifications of the microtubule network, which fully abrogated mechano-sensitivity (as shown by $Ca^{2+}$ influx, CaMKII phosphorylation, and sclerostin downregulation), residual FSS-induced $Ca^{2+}$ influx with pharmacologic or molecular inhibition of TRPV4 was still observed. While several other $Ca^{2+}$ influx pathways have been identified in osteocytes, the present results suggested that these pathways are likely activated downstream or in parallel to the initial $Ca^{2+}$ influx through TRPV4. Indeed, oscillating $Ca^{2+}$ waves can be driven by ATP release and purinergic receptor activation in mechano-activated osteocytes (52-54) as well as $Ca^{2+}$ influx through T-type voltage gated calcium channels (41, 55).

Regardless, the present invention shows that TRPV4 activity is obligated even if other $Ca^{2+}$ pathways are also involved in mechano-sensing.

The involvement of TRPV4 in osteocyte mechano-sensing was consistent with the demonstration of TRPV4 as a mediator of mechanically-induced $Ca^{2+}$ influx in the primary cilia of bone cells (37). Likewise, TRPV4 plays an important role in chondrocyte mechanotransduction, as blocking TRPV4 prevents an anabolic response to load, while activating the receptor mimics load (56). In contrast, global TRPV4 knockout mice have increased bone mass; however, the interpretation is complicated by a severe osteoclast defect that contributes to the skeletal phenotype (57). Despite higher trabecular and cortical bone mass, male TRPV4 knockout mice have reduced bone matrix mineralization, increased cortical porosity, a lower ultimate stress and reduced elastic modulus (58). Regardless, TRPV4 plays a role in the skeleton as numerous gain of function TRPV4 mutations cause skeletal dysplasias with a breadth of severity (59). A SNP in the human TRPV4 locus was associated with a 30% increase risk of non-vertebral fractures in males in the Rotterdam study and was confirmed in subsequent meta-analysis (58).

Consistent with reports in striated muscle (39, 49, 51), the present invention showed an important role for mechano-activated, NOX2-dependent ROS in the osteocyte response to fluid shear stress. $p47^{phox}$ global knockout mice, a subunit of the NOX2 enzyme, have decreased bone mass and strength in aged adult mice, due to deficits in osteoblast differentiation, osteoblast number, and accelerated cell senescence (60). This phenotype is not observed in 6-week-old mice, which have increased bone mass. Whether or not changes in mechano-sensing or sclerostin bioavailability contribute to the worsening skeletal phenotype have not been assessed nor have these mice been studied in the context of mechanical loading.

The present invention aligns with reports that implicate microtubules in mechanotransduction as well as observations that the microtubule network of osteocytes remodels and reorients itself in response to fluid shear stress (34-36). It is reasonable to speculate that the fluid shear stress-dependent remodeling of microtubules is itself a mechano-adaptation event that adjusts the homeostatic set point for mechanotransduction. As mentioned above, the present invention illustrates a unifying basis for how various known mechano-sensitive elements (such as primary cilia, cell processes, integrin-mediated mechanosomes, and connexin43 hemichannels) may integrate mechanical signals into biological responses through the cytoskeleton. Further, the present invention mechanistically linked the mechano-activated $Ca^{2+}$ influx to sclerostin downregulation. The implications of ROS as a fundamental driver of mechano-responses may also extrapolate to known deficits in bone mechano-responsiveness in conditions of aberrant redox buffering capacity, including aging (61).

In summary, the present invention defined the MT-dependent mechanotransduction pathway linking FSS to NOX2-generated ROS that elicits TRPV4 dependent $Ca^{2+}$ influx signals that activate CaMKII to decrease sclerostin protein in osteocytes. Given the fundamental nature of osteocyte mechano-responsiveness to bone turnover throughout the life span, these mechanistic insights may provide a new perspective for understanding diseases and conditions that manifest through altered skeletal structure and properties. Moreover, given the impact of the MT network on the fundamental regulation of $Ca^{2+}$ signaling and sclerostin production in osteocytes, the present invention shows that the MT network is a target for manipulating the osteocyte response to mechanical cues for therapeutic interventions in bone.

The present invention shows that microtubule density decreases the function of bone by preventing the destruction of sclerostin protein, an inhibitor of bone mass. Treatment with colchicine to reduce microtubule density reduced sclerostin and improved bone formation rates in aged mice, as shown by DEXA and CT measures of accumulated bone. Because sclerostin also regulates white adipose tissue, fat accumulation in these tissues was examined. As predicted, treating with colchicine to reduce microtubule density reduced fat mass in white adipose depots. Correspondingly similar age dependent increases in microtubule density occur in muscle and impair its function, treatment with colchicine improved muscle power.

The following references are cited herein.

1. Dallas, et al., Endocr Rev 34, 658-690 (2013); published online EpubOct (10.1210/er.2012-1026).
2. Klein-Nulend, et al., Bone 54, 182-190 (2013); published online EpubJun (10.1016/j.bone.2012.10.013).
3. Schaffler, et al., Calcif Tissue Int 94, 5-24 (2014); published online EpubJan (10.1007/s00223-013-9790-y).
4. Li, et al., J Biol Chem 280, 19883-19887 (2005); published online EpubMay 20 (10.1074/jbc.M413274200).
5. Lin, et al., J Bone Miner Res 24, 1651-1661 (2009); published online EpubOct (10.1359/jbmr.090411).
6. Robling, et al., J Biol Chem 283, 5866-5875 (2008); published online EpubFeb 29 (10.1074/jbc.M705092200).
7. Tu, et al., Bone 50, 209-217 (2012); published online EpubJan (10.1016/j.bone.2011.10.025).
8. Balemans, et al., J Med Genet 39, 91-97 (2002); published online EpubFeb
9. Balemans, et al., Hum Mol Genet 10, 537-543 (2001); published online EpubMar 1.
10. Li, et al., J Bone Miner Res 23, 860-869 (2008); published online EpubJun (10.1359/jbmr.080216).
11. Compton, et al., J Bone Joint Surg Am 96, 1659-1668 (2014); published online EpubOct 1 (10.2106/JBJS.M.01096).
12. McClung, et al., N Engl J Med 370, 412-420 (2014); published online EpubJan 30 (10.1056/NEJMoa1305224).
13. Pavalko, et al., J Cell Biochem 88, 104-112 (2003); published online EpubJan 1 (10.1002/jcb.10284).
14. Thi, et al., Proc Natl Acad Sci USA 110, 21012-21017 (2013); published online EpubDec 24 (10.1073/pnas.1321210110).
15. Wu, et al., Proc Natl Acad Sci USA 110, 12096-12101 (2013); published online EpubJul 16 (10.1073/pnas.1310003110).
16. Nguyen, et al., Bone 54, 196-204 (2013); published online EpubJun (10.1016/j.bone.2012.11.016).
17. Batra et al., Proc Natl Acad Sci USA 109, 3359-3364 (2012); published online EpubFeb 28 (10.1073/pnas.1115967109).
18. Pavalko et al., Am J Physiol 275, C1591-1601 (1998); published online EpubDec
19. Vignaud, et al., Trends Cell Biol 22, 671-682 (2012); published online EpubDec (10.1016/j.tcb.2012.08.012).
20. Lopez, et al., Biochim Biophys Acta 1853, 3015-3024 (2015); published online EpubNov (10.1016/j.bbamcr.2015.07.016).
21. Ohashi, et al., J Biochem, (2017); published online EpubJan 12 (10.1093/jb/mvw082).

22. Song et al., Trends Cell Biol 25, 125-136 (2015); published online EpubMar (10.1016/j.tcb.2014.10.004).
23. Wloga et al., Cold Spring Harb Perspect Biol, (2016); published online EpubDec 21 (10.1101/cshperspect.a028159).
24. Robison et al., Science 352, aaf0659 (2016); published online EpubApr 22 (10.1126/science.aaf0659).
25. Kreitzer et al., Mol Biol Cell 10, 1105-1118 (1999); published online EpubApr
26. Liao et al., J Biol Chem 273, 9797-9803 (1998); published online EpubApr 17
27. Spatz et al., J Biol Chem 290, 16744-16758 (2015); published online EpubJul 3 (10.1074/jbc.M114.628313).
28. Babich et al., Immunol Rev 256, 80-94 (2013); published online EpubNov (10.1111/imr.12123).
29. Oka et al., J Immunol 174, 4584-4589 (2005); published online EpubApr 15
30. Ward et al., Antioxid Redox Signal 20, 929-936 (2014); published online EpubFeb 20 (10.1089/ars.2013.5517).
31. Plotkin et al., Am J Physiol Cell Physiol 289, C633-643 (2005); published online EpubSep (10.1152/ajpcell.00278.2004).
32. Toma et al., J Bone Miner Res 12, 1626-1636 (1997); published online EpubOct (10.1359/jbmr.1997.12.10.1626).
33. N. Rosenberg, Hum Exp Toxicol 22, 271-274 (2003); published online EpubMay.
34. Myers et al., Biochem Biophys Res Commun 364, 214-219 (2007); published online EpubDec 14 (10.1016/j.bbrc.2007.09.109).
35. Espinha et al., Cytoskeleton (Hoboken) 71, 435-445 (2014); published online EpubJul (10.1002/cm.21183).
36. Gardinier et al., Cell Mol Bioeng 2, 133-143 (2009); published online EpubMar 01 (10.1007/s12195-008-0038-2).
37. Lee et al., Cilia 4, 7 (2015)10.1186/si3630-015-0016-y).
38. Janke et al., Nat Rev Mol Cell Biol 12, 773-786 (2011); published online EpubNov 16 (10.1038/nrm3227).
39. Kerr et al., Nature communications 6, 8526 (2015) 10.1038/ncomms9526). 72
40. Fonrose et al., Cancer research 67, 3371-3378 (2007); published online EpubApr 1 (10.1158/0008-5472.CAN-06-3732).
41. Brown et al., Bone 88, 56-63 (2016); published online EpubJul (10.1016/j.bone.2016.04.018).
42. Seref-Ferlengez et al., PLoS One 11, e0155107 (2016) 10.1371/journal.pone.0155107).
43. Thompson et al., J Bone Miner Res 26, 2125-2139 (2011); published online EpubSep (10.1002/jbmr.437).
44. Suzuki et al., J Biol Chem 278, 51448-51453 (2003); published online EpubDec 19 (10.1074/jbc.M308212200).
45. Wei et al., Neurosci Lett 534, 344-350 (2013); published online EpubFeb 8 (10.1016/j.neulet.2012.12.003).
46. Goswami et al., PLoS One 5, e11654 (2010) 10.1371/journal.pone.0011654).
47. Suresh et al., Am J Physiol Lung Cell Mol Physiol 309, L1467-1477 (2015); published online EpubDec 15 (10.1152/ajplung.00275.2015).
48. Wegierski et al., J Biol Chem 284, 2923-2933 (2009); published online EpubJan 30 (10.1074/jbc.M805357200).
49. Prosser et al., Science 333, 1440-1445 (2011); published online EpubSep 9 (10.1126/science.1202768).
50. Browning et al., Annu Rev Physiol 74, 403-424 (2012) 10.1146/annurev-physiol-020911-153324).
51. Khairallah et al., Science signaling 5, ra56 (2012); published online EpubAug 7 (10.1126/scisignal.2002829).
52. Kringelbach et al., Cell Signal 27, 2401-2409 (2015); published online EpubDec (10.1016/j.cellsig.2015.08.016).
53. Jing et al., FASEB J 28, 1582-1592 (2014); published online EpubApr (10.1096/fj.13-237578).
54. Genetos et al., J Cell Physiol 212, 207-214 (2007); published online EpubJul (10.1002/jcp.21021).
55. Lu et al., J Bone Miner Res 27, 563-574 (2012); published online EpubMar (10.1002/jbmr.1474).
56. O'Conor et al., Proc Natl Acad Sci USA 111, 1316-1321 (2014); published online EpubJan 28 (10.1073/pnas.1319569111).
57. Masuyama et al., Cell Metab 8, 257-265 (2008); published online EpubSep (10.1016/j.cmet.2008.08.002).
58. van der Eerden et al., Bone 57, 443-454 (2013); published online EpubDec (10.1016/j.bone.2013.09.017).
59. Leddy et al., Rare Dis 2, e962971 (2014)10.4161/2167549X.2014.962971).
60. Chen et al., J Biol Chem 290, 14692-14704 (2015); published online EpubJun 05 (10.1074/jbc.M114.633461).
61. H. Razi et al., J Bone Miner Res 30, 1864-1873 (2015); published online EpubOct (10.1002/jbmr.2528).
62. Gupta et al., Cell Signal 28, 1048-1057 (2016); published online EpubMay 6 (10.1016/j.cellsig.2016.04.014).
63. Lyons et al., J Biomech 49, 4173-4179 (2016); published online EpubDec 08 (10.1016/j.jbiomech.2016.11.051).
64. Hanley et al., J Cell Sci 117, 2503-2511 (2004); published online EpubMay 15 (10.1242/jcs.01088).
65. Raman et al., J Cell Sci 124, 1903-1910 (2011); published online EpubJun 01 (10.1242/jcs.079814).
66. Hung et al., Cell Rep 15, 1430-1441 (2016); published online EpubMay 17 (10.1016/j.celrep.2016.04.035).
67. Hebert et al., J Cell Biochem 114, 2542-2550 (2013); published online EpubNov (10.1002/jcb.24603).
68. Moorer et al., J Cell Sci 130, 531-540 (2017); published online EpubFeb 01 (10.1242/jcs.197285).
69. Moorer et al., Am J Physiol Cell Physiol 311, C839-C845 (2016); published online EpubDec 01 (10.1152/ajpcell.00218.2016).
70. Niger et al., J Bone Miner Res 28, 1468-1477 (2013); published online EpubJun (10.1002/jbmr.1867).
71. Lyons et al. Sci Signal. 10(506), 21 Nov. 2017, PMID: 29162742.
72. Kim et al. PNAS, 2017, PMID: 2922980.

What is claimed is:

1. A method for treating osteoporosis in a subject, comprising:

administering to the subject an amount of a microtubule disrupting drug pharmacologically effective to treat osteoporosis, wherein the microtubule disrupting drug is colchicine.

2. The method of claim 1, further comprising administering to the subject an anti-sclerostin agent.

3. The method of claim 2, wherein the anti-sclerostin agent is a monoclonal antibody or an antigen-binding fragment thereof.

4. The method of claim 2, wherein the anti-sclerostin agent is romosozumab or blosozumab.

5. The method of claim 1, further comprising administering to the subject at least one of a parathyroid hormone agonist, a bisphosphonate, an estrogen mimic, or a selective estrogen receptor modulator.

6. The method of claim 1, wherein the osteoporosis is osteoporosis in men regional migratory osteoporosis, or regional osteoporosis.

7. A method for treating osteoporosis in a subject, comprising:

administering to the subject one or more times an amount of a microtubule disrupting drug, or a combination of a microtubule disrupting drug and a microtubule stabilizing drug, each pharmacologically effective to treat osteoporosis, wherein the microtubule disrupting drug is colchicine.

8. The method of claim 7, wherein the microtubule stabilizing drug is a taxane or eothinolone.

9. The method of claim 7, wherein the microtubule stabilizing drug is a taxane.

10. A method for increasing bone mass in a subject who suffers from a bone-related disorder associated with aging, the method comprising:

administering to the subject one or more times an amount of a microtubule disrupting drug pharmacologically effective to decrease sclerostin in the subject, wherein the microtubule disrupting drug is colchicine.

11. The method of claim 10, further comprising administering to the subject at least once a microtubule stabilizing drug or an anti-sclerostin agent or a combination thereof.

12. The method of claim 11, wherein the microtubule stabilizing drug is a taxane or eothinolone.

13. The method of claim 11, wherein the anti-sclerostin agent is a monoclonal antibody or an antigen-binding fragment thereof.

14. The method of claim 13, wherein the anti-sclerostin agent is romosozumab or blosozumab.

15. The method of claim 10, wherein the bone-related disorder associated with aging is osteoporosis.

* * * * *